(12) United States Patent
Igasaki et al.

(10) Patent No.: US 11,612,956 B2
(45) Date of Patent: Mar. 28, 2023

(54) LASER LIGHT RADIATION DEVICE AND LASER LIGHT RADIATION METHOD

(71) Applicant: HAMAMATSU PHOTONICS K.K., Hamamatsu (JP)

(72) Inventors: Yasunori Igasaki, Hamamatsu (JP); Aiko Nakagawa, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 407 days.

(21) Appl. No.: 16/083,066

(22) PCT Filed: Mar. 3, 2017

(86) PCT No.: PCT/JP2017/008578
§ 371 (c)(1),
(2) Date: Sep. 7, 2018

(87) PCT Pub. No.: WO2017/154791
PCT Pub. Date: Sep. 14, 2017

(65) Prior Publication Data
US 2019/0126393 A1 May 2, 2019

(30) Foreign Application Priority Data
Mar. 10, 2016 (JP) .............................. JP2016-047156

(51) Int. Cl.
*B23K 26/064* (2014.01)
*B23K 26/035* (2014.01)
(Continued)

(52) U.S. Cl.
CPC ............ *B23K 26/064* (2015.10); *B23K 26/00* (2013.01); *B23K 26/0006* (2013.01);
(Continued)

(58) Field of Classification Search
CPC .................................................. B23K 26/064
See application file for complete search history.

(56) References Cited

U.S. PATENT DOCUMENTS

2005/0070035 A1* 3/2005 Yazaki .............. H01L 21/02686
438/22
2005/0161436 A1* 7/2005 Yoshimura ......... B23K 26/0676
216/87
(Continued)

FOREIGN PATENT DOCUMENTS

CN 104471465 A 3/2015
CN 105102179 A 11/2015
(Continued)

OTHER PUBLICATIONS

International Preliminary Report on Patentability dated Sep. 20, 2018 for PCT/JP2017/008578.

*Primary Examiner* — Andrew D Graham
(74) *Attorney, Agent, or Firm* — Faegre Drinker Biddle & Reath LLP

(57) ABSTRACT

A laser light irradiation device includes: a laser light source; a spatial light modulator including a display unit configured to display a phase pattern; an objective lens configured to condense a laser light emitted from the spatial light modulator at the object; an image-transfer optical system configured to transfer an image of the laser light on the display unit to an entrance pupil plane of the objective lens; a reflected light detector configured to detect reflected light of the laser light which is incident in the object and reflected by an opposite surface opposite to a laser light entrance surface; and a controller configured to control the phase pattern. When the reflected light detector detects the reflected light, the controller displays a reflected light aberration correction pattern which is the phase pattern correcting aberration generated in the event of the laser light being transmitted (Continued)

through the object having twice the predetermined thickness.

17 Claims, 27 Drawing Sheets

(51) Int. Cl.
  B23K 26/00 (2014.01)
  G02F 1/13 (2006.01)
  B23K 26/53 (2014.01)
  B23K 26/70 (2014.01)
  B23K 26/03 (2006.01)
  B23K 26/08 (2014.01)
  H01L 21/268 (2006.01)
  H01L 21/67 (2006.01)
  H01L 21/78 (2006.01)
  H01L 41/338 (2013.01)
  B23K 103/00 (2006.01)
  B23K 101/40 (2006.01)

(52) U.S. Cl.
  CPC .......... *B23K 26/032* (2013.01); *B23K 26/035* (2015.10); *B23K 26/083* (2013.01); *B23K 26/53* (2015.10); *B23K 26/705* (2015.10); *G02F 1/13* (2013.01); *H01L 21/268* (2013.01); *H01L 21/67092* (2013.01); *H01L 21/67115* (2013.01); *H01L 21/67259* (2013.01); *H01L 21/78* (2013.01); *H01L 41/338* (2013.01); *B23K 2101/40* (2018.08); *B23K 2103/56* (2018.08)

(56) References Cited

U.S. PATENT DOCUMENTS

| | | | |
|---|---|---|---|
| 2007/0151963 A1* | 7/2007 | Tanaka | B23K 26/40 257/E29.151 |
| 2007/0262264 A1* | 11/2007 | Hasegawa | G02B 21/0032 250/458.1 |
| 2008/0013170 A1* | 1/2008 | Tanaka | B23K 26/064 359/434 |
| 2010/0197116 A1* | 8/2010 | Shah | B23K 26/40 219/121.68 |
| 2010/0295836 A1* | 11/2010 | Matsumoto | G02F 1/13318 345/211 |
| 2011/0000897 A1 | 1/2011 | Nakano et al. | |
| 2011/0193269 A1* | 8/2011 | Ito | G02B 21/0032 264/400 |
| 2011/0298156 A1* | 12/2011 | Hooper | B23K 26/0622 264/400 |
| 2011/0300691 A1* | 12/2011 | Sakamoto | C03B 33/0222 257/E21.599 |
| 2011/0316200 A1* | 12/2011 | Iwaki | B23K 26/064 264/400 |
| 2012/0119334 A1* | 5/2012 | Nakagawa | B23K 26/53 257/E23.179 |
| 2016/0052088 A1* | 2/2016 | Kawaguchi | B23K 26/53 219/121.75 |
| 2017/0113301 A1* | 4/2017 | Sakamoto | B23K 26/0676 |
| 2017/0216973 A1* | 8/2017 | Sakamoto | B23K 26/083 |
| 2019/0047084 A1* | 2/2019 | Okuma | B23K 26/0648 |

FOREIGN PATENT DOCUMENTS

| | | |
|---|---|---|
| JP | 3878758 B2 | 2/2007 |
| JP | 2009-082966 A | 4/2009 |
| JP | 2011-51011 A | 3/2011 |
| JP | 2015-226012 A | 12/2015 |
| KR | 1020090033817 A | 4/2009 |
| KR | 101013286 B1 | 2/2011 |
| KR | 2015-0133709 A | 11/2015 |
| WO | WO-2013/153371 A1 | 10/2013 |

* cited by examiner

Fig.17
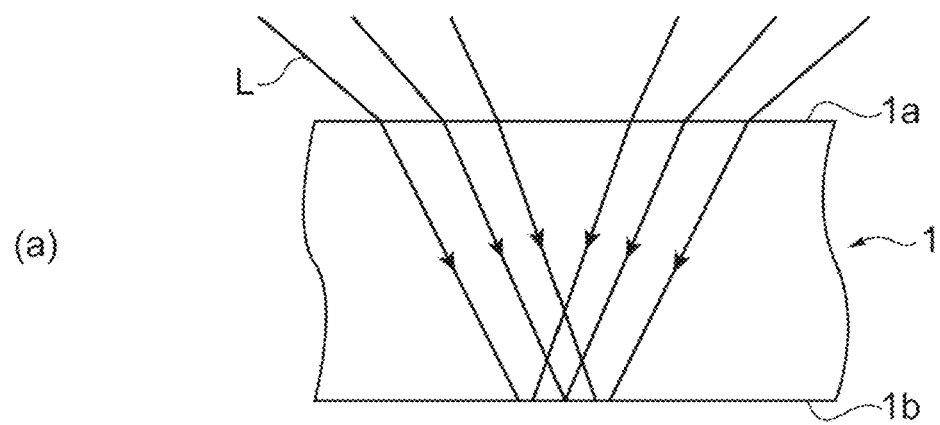
(a)
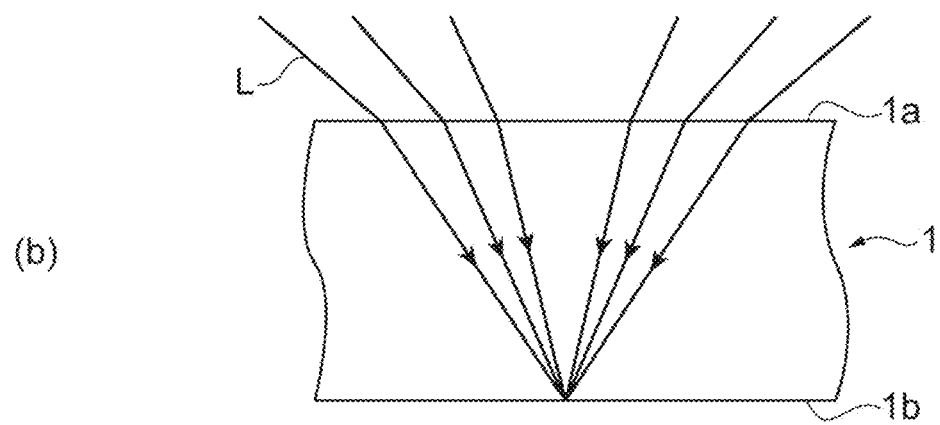
(b)
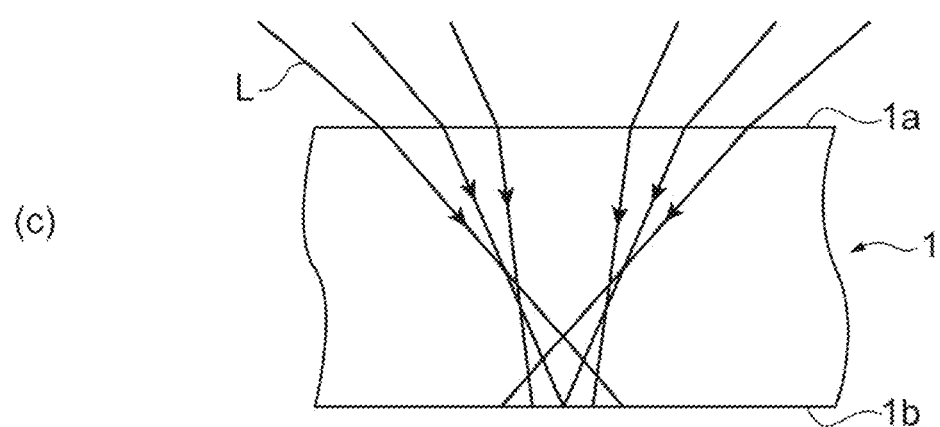
(c)

*Fig.18*
(a)
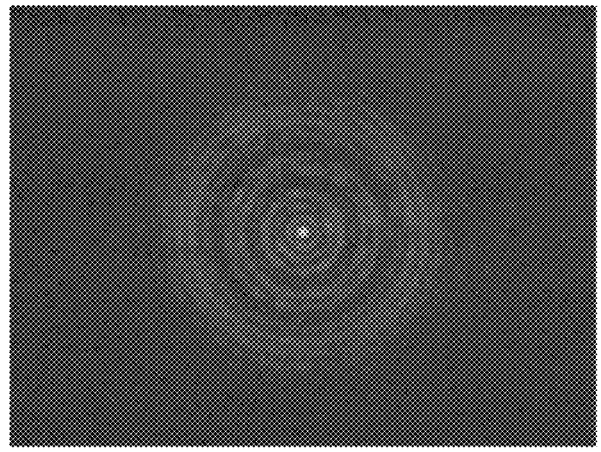
(b)
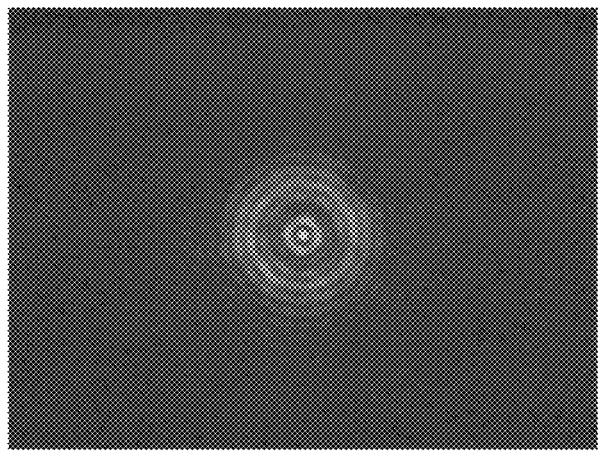
(c)
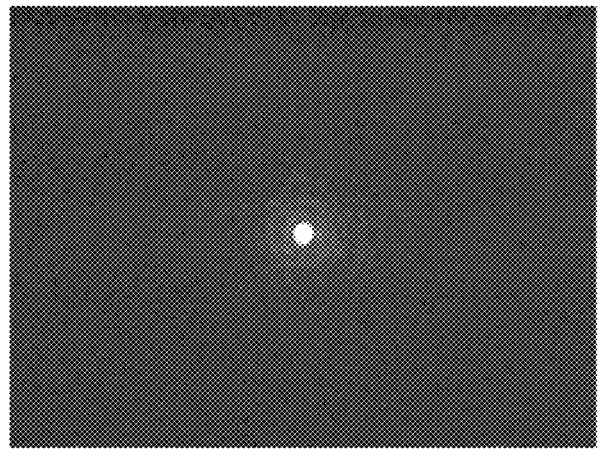

Fig. 25

| DEPTH (μm) | −2 FORWARD PATH | −2 RETURNING PATH | −1 FORWARD PATH | −1 RETURNING PATH | 0 FORWARD PATH | 0 RETURNING PATH | 1 FORWARD PATH | 1 RETURNING PATH | 2 FORWARD PATH | 2 RETURNING PATH |
|---|---|---|---|---|---|---|---|---|---|---|
| 676 | EXCELLENT | EXCELLENT | EXCELLENT | EXCELLENT | EXCELLENT | EXCELLENT | EXCELLENT | EXCELLENT | EXCELLENT | EXCELLENT |
| 668 | EXCELLENT | EXCELLENT | EXCELLENT | EXCELLENT | EXCELLENT | EXCELLENT | EXCELLENT | EXCELLENT | EXCELLENT | EXCELLENT |
| 660 | GOOD | EXCELLENT | EXCELLENT | EXCELLENT | EXCELLENT | EXCELLENT | EXCELLENT | EXCELLENT | EXCELLENT | EXCELLENT |
| 652 | GOOD | GOOD | EXCELLENT | EXCELLENT | EXCELLENT | EXCELLENT | EXCELLENT | EXCELLENT | EXCELLENT | EXCELLENT |
| 644 | GOOD | GOOD | EXCELLENT | EXCELLENT | EXCELLENT | EXCELLENT | EXCELLENT | EXCELLENT | GOOD | GOOD |
| 636 | GOOD | GOOD | EXCELLENT | GOOD | EXCELLENT | EXCELLENT | EXCELLENT | EXCELLENT | GOOD | GOOD |
| 628 | WRONG | WRONG | GOOD | GOOD | EXCELLENT | EXCELLENT | GOOD | GOOD | WRONG | WRONG |
| 620 | WRONG | WRONG | GOOD | GOOD | EXCELLENT | EXCELLENT | GOOD | GOOD | WRONG | WRONG |

Y DIRECTION (PIXEL)

Fig.26

| DEPTH (μm) | -2 FORWARD PATH | -2 RETURNING PATH | -1 FORWARD PATH | -1 RETURNING PATH | 0 FORWARD PATH | 0 RETURNING PATH | 1 FORWARD PATH | 1 RETURNING PATH | 2 FORWARD PATH | 2 RETURNING PATH |
|---|---|---|---|---|---|---|---|---|---|---|
| 708 | EXCELLENT | GOOD | EXCELLENT | EXCELLENT | EXCELLENT | EXCELLENT | EXCELLENT | EXCELLENT | WRONG | EXCELLENT |
| 704 | EXCELLENT | WRONG | EXCELLENT | EXCELLENT | EXCELLENT | EXCELLENT | EXCELLENT | EXCELLENT | WRONG | EXCELLENT |
| 700 | EXCELLENT | WRONG | EXCELLENT | EXCELLENT | EXCELLENT | EXCELLENT | EXCELLENT | EXCELLENT | WRONG | EXCELLENT |
| 696 | GOOD | WRONG | GOOD | WRONG | GOOD | GOOD | GOOD | GOOD | WRONG | GOOD |
| 692 | GOOD | WRONG | WRONG | WRONG | GOOD | GOOD | GOOD | GOOD | WRONG | GOOD |
| 688 | GOOD | WRONG | WRONG | WRONG | GOOD | WRONG | GOOD | WRONG | WRONG | WRONG |
| 684 | WRONG | WRONG | WRONG | WRONG | WRONG | WRONG | WRONG | WRONG | WRONG | WRONG |
| 680 | WRONG | WRONG | WRONG | WRONG | WRONG | WRONG | WRONG | WRONG | WRONG | WRONG |

X DIRECTION (PIXEL)

LASER LIGHT RADIATION DEVICE AND LASER LIGHT RADIATION METHOD

TECHNICAL FIELD

One aspect of the present invention relates to a laser light irradiation device and a laser light irradiation method.

BACKGROUND ART

Conventionally, as an example of a laser light irradiation device for irradiating an object with laser light, a device disclosed in Patent Literature 1 is described. In such a laser light irradiation device, laser light generated by a laser light source is modulated by a spatial light modulator and then collected on an object by an objective lens.

CITATION LIST

Patent Literature

Patent Literature 1: Japanese Unexamined Patent Publication No. 2011-51011

SUMMARY OF INVENTION

Technical Problem

In the laser light irradiation device, the image of the laser light on a display unit of the spatial light modulator is transferred onto an entrance pupil plane of the objective lens by an image-transfer optical system such as a $4f$ optical system. Here, when the center position of the image of the laser light transferred onto the entrance pupil plane of the objective lens does not coincide with the center position of the entrance pupil plane, there is a possibility that, for example, the beam intensity center of the laser light focused on the object may be shifted, and the processing quality (the quality of the object after the laser light irradiation) may deteriorate.

Therefore, it is an object of one aspect of the present invention to provide a laser light irradiation device and a laser light irradiation method, capable of grasping a shift between the center position of an image of laser light transferred onto an entrance pupil plane of an objective lens by an image-transfer optical system and a center position of the entrance pupil plane.

Solution to Problem

A laser light irradiation device according to one aspect of the present invention is a laser light irradiation device for irradiating an object having a predetermined thickness with laser light, the laser light irradiation device including: a laser light source configured to generate the laser light; a spatial light modulator including a display unit configured to display a phase pattern, the spatial light modulator configured to cause the laser light generated by the laser light source to enter the display unit, modulate the laser light according to the phase pattern, and emit the laser light from the display unit; an objective lens configured to condense the laser light emitted from the spatial light modulator at the object; an image-transfer optical system configured to transfer an image of the laser light on the display unit of the spatial light modulator to an entrance pupil plane of the objective lens; a reflected light detector configured to detect reflected light of the laser light which is incident in the object and reflected by an opposite surface opposite to a laser light entrance surface; and a controller configured to control at least the phase pattern to be displayed on the display unit, wherein when the reflected light detector detects the reflected light, the controller displays, on the display unit, a reflected light aberration correction pattern which is the phase pattern correcting aberration generated in the event of the laser light being transmitted through the object having twice the predetermined thickness.

In the laser light irradiation device, the reflected light of the laser light incident from the laser light entrance surface of the object and reflected by the opposite surface is detected by the reflected light detector. At this time, the aberration generated in the reflected light due to transmission through the object can be modulated and corrected with the reflected light aberration correction pattern of the reflected light spatial light modulator. Here, it is found that when there is a shift between the center position of the image of the laser light transferred onto the entrance pupil plane and the center position of the entrance pupil plane (hereinafter also simply referred to as "image-transfer position shift"), for example, the influence of aberration such as coma aberration easily appears on the reflected light detected by the reflected light detector since the laser light is not correctly condensed by the objective lens, as compared with the case in which there is no such image-transfer position shift. Therefore, it is possible to grasp the image-transfer position shift based on the detection result of detecting the reflected light.

The laser light irradiation device according to one aspect of the present invention may further include a position determining unit configured to determine whether there is a shift between a center position of the entrance pupil plane and a center position of the image of the laser light transferred onto the entrance pupil plane by the image-transfer optical system, based on a detection result of the reflected light detector. According to this configuration, it is possible to automatically determine the presence or absence of the image-transfer position shift.

In the laser light irradiation device according to one aspect of the present invention, the reflected light detector may include a camera configured to capture an image including a point image of the reflected light, and when the point image of the reflected light in the image captured by the camera is not a rotationally symmetric optical image, the position determining unit may determine that there is the shift. It is found that when there is no image-transfer position shift, the point image of the reflected light captured by the camera becomes the optical image to be rotated, and when there is the image-transfer position shift, it is difficult to form the rotationally symmetric optical image by the influence of coma aberration or the like. Therefore, when the point image of the reflected light is not a rotationally symmetric optical image, the position determining unit determines that there is an image-transfer position shift, thereby accurately determining the presence or absence of the image-transfer position shift.

In the laser light irradiation device according to one aspect of the present invention, the reflected light detector may include a wavefront sensor configured to detect a wavefront of the reflected light, and when the wavefront of the reflected light detected by the wavefront sensor is not a plane, the position determining unit may determine that there is the shift. It is found that the reflected light becomes a plane wave when there is no image-transfer position shift, and it is hard to form a plane wave when there is the image-transfer position shift. Therefore, when the wavefront of the reflected light detected by the wavefront sensor is not planar, the position determining unit determines that there is an image-transfer position shift, thereby accurately determining the presence or absence of the image-transfer position shift.

The laser light irradiation device according to one aspect of the present invention may further include a position adjustment unit configured to offset a reference position serving as a reference when the phase pattern is displayed on the display unit, based on the detection result of the reflected light detector. By offsetting the reference position from the detection result of the reflected light detector, it is possible to adjust the position of the image of the laser light that has been transferred onto the entrance pupil plane so as to reduce the image-transfer position shift.

In the laser light irradiation device according to one aspect of the present invention, the reflected light detector may include a camera configured to capture an image including a point image of the reflected light, and the position adjustment unit may offset the reference position such that the point image of the reflected light in the image captured by the camera becomes a rotationally symmetric optical image. As described above, it is found that when there is no image-transfer position shift, the point image of the reflected light captured by the camera becomes the optical image to be rotated. Therefore, by offsetting the reference position such that the point image of the reflected light becomes a rotationally symmetric optical image, it is possible to adjust the center position of the image of the laser light transferred onto the entrance pupil plane so as to be aligned with the center position of the entrance pupil plane, thereby reducing the image-transfer position shift.

In the laser light irradiation device according to one aspect of the present invention, the reflected light detector may include a wavefront sensor configured to detect a wavefront of the reflected light, and the position adjustment unit may offset the reference position such that the wavefront of the reflected light detected by the wavefront sensor becomes a plane. As described above, it is found that when there is no image-transfer position shift, the reflected light becomes a plane wave. Therefore, by offsetting the reference position such that the wavefront of the reflected light detected by the wavefront sensor becomes a plane, it is possible to adjust the center position of the image of the laser light transferred onto the entrance pupil plane so as to be aligned with the center position of the entrance pupil plane, thereby reducing the image-transfer position shift.

The laser light irradiation device according to one aspect of the present invention may further include a moving mechanism configured to move at least one of the objective lens and the object, wherein the controller may execute: a first process of displaying the reflected light aberration correction pattern on the display unit; a second process of moving, by the moving mechanism, at least one of the objective lens and the object to a position at which the reflected light detector can detect the reflected light; a third process of, in a state in which the reflected light aberration correction pattern is displayed on the display unit by the first process after the second process, generating the laser light from the laser light source to irradiate the object and acquiring the detection result of the reflected light detector detected according to the irradiation; and a fourth process of repeating the third process one or more times while changing the position of the reflected light aberration correction pattern on the display unit and acquiring a plurality of detection results of the reflected light detector, and the position adjustment unit may calculate an optical axis center of the display unit based on the plurality of detection results of the reflected light detector and offset the reference position to the optical axis center. In this case, it is possible to specifically realize adjustment for reducing the image-transfer position shift.

A laser light irradiation method according to one aspect of the present invention is a laser light irradiation method for irradiating an object having a predetermined thickness with laser light by using a laser light irradiation device, wherein laser light irradiation device includes: a laser light source configured to generate the laser light; a spatial light modulator including a display unit configured to display a phase pattern, the spatial light modulator configured to cause the laser light generated by the laser light source to enter the display unit, modulate the laser light according to the phase pattern, and emit the laser light from the display unit; an objective lens configured to condense the laser light emitted from the spatial light modulator at the object; an image-transfer optical system configured to transfer an image of the laser light on the display unit of the spatial light modulator to an entrance pupil plane of the objective lens; and a reflected light detector configured to detect reflected light of the laser light which is incident in the object and reflected by an opposite surface opposite to a laser light entrance surface, the laser light irradiation method including: a first step of displaying, on the display unit, a reflected light aberration correction pattern which is the phase pattern correcting aberration generated in the event of the laser light being transmitted through the object having twice the predetermined thickness; a second step of, in a state in which the reflected light aberration correction pattern is displayed on the display unit by the first step, generating the laser light from the laser light source to irradiate the object and detecting reflected light of the laser light by the reflected light detector according to the irradiation; and a third step of offsetting a reference position serving as a reference when the phase pattern is displayed on the display unit after the second step, based on a detection result of the reflected light detector.

As described above, it is found that when there is the image-transfer position shift, the influence of aberration such as coma aberration easily appears on the reflected light detected by the reflected light detector, as compared to the case in which there is no image-transfer position shift. Therefore, it is possible to grasp the image-transfer position shift by the detection result of the reflected light detected in the second step. Further, by offsetting the reference position from the detection result of the reflected light detector in the third step, the position of the image of the laser light transferred onto the entrance pupil plane can be adjusted so as to reduce the image-transfer position shift.

Advantageous Effects of Invention

According to one aspect of the present invention, the laser light irradiation device and laser light irradiation method can be provided capable of grasping the shift between the center position of the image of the laser light transferred onto the entrance pupil plane of the objective lens by the image-transfer optical system and the center position of the entrance pupil plane.

BRIEF DESCRIPTION OF DRAWINGS

FIG. 17 is a schematic sectional view for explaining each condensing state at the time of rear face reflection of laser light.

FIG. 18 is a photograph showing an example of a point image captured by an observation camera in each condensing state of FIG. 17.

FIG. 25 is a table showing a relationship between a reference position and a laser processing result.

FIG. 26 is another table showing a relationship between a reference position and a laser processing result.

DESCRIPTION OF EMBODIMENTS

Figure 1:
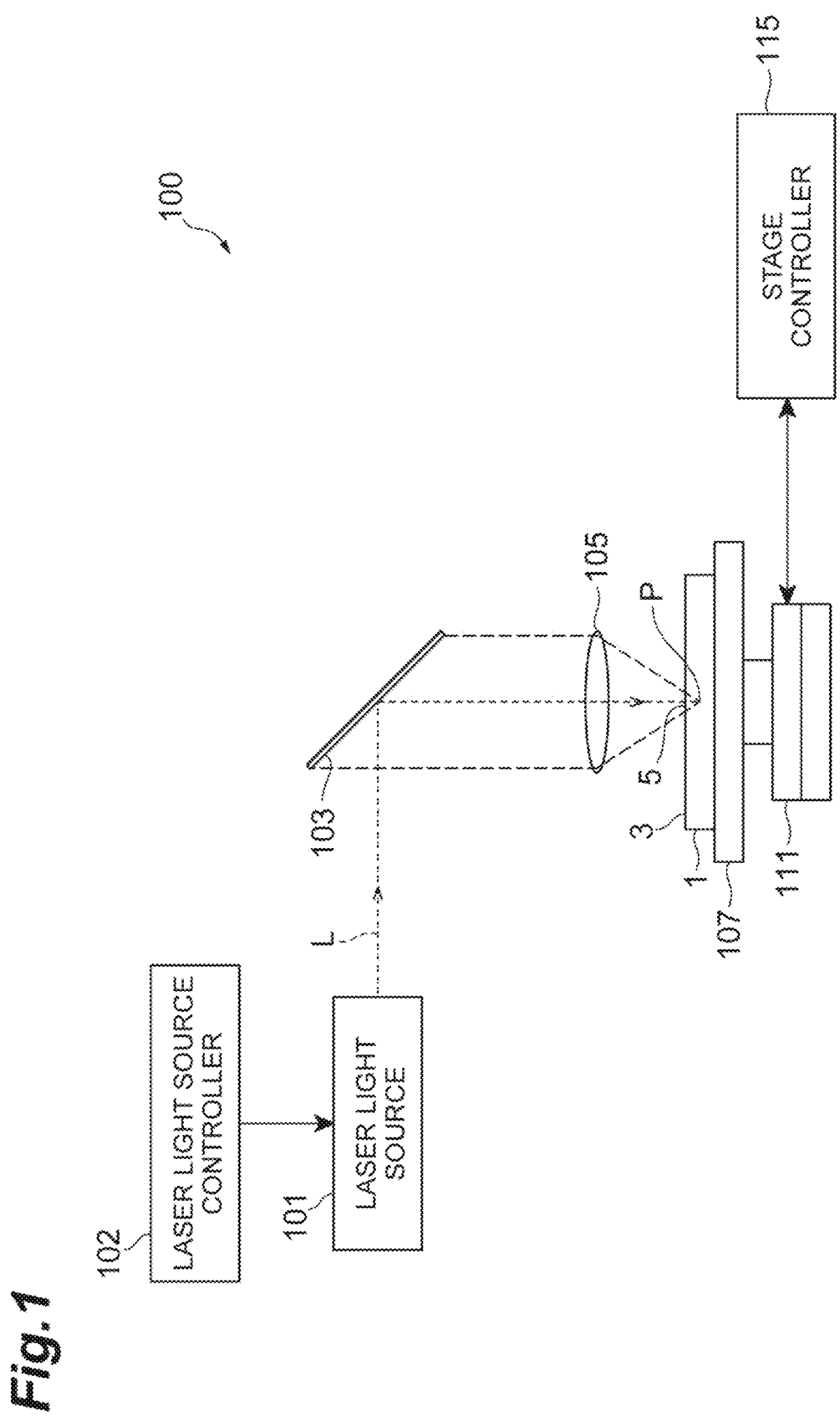
FIG. 1 is a schematic configuration diagram of a laser processing device used for forming a modified region.

Hereinafter, embodiments will be explained in detail with reference to drawings. In the drawings, the same or equivalent parts will be denoted by the same reference signs, without redundant description.

A laser processing device (laser light irradiation device) according to an embodiment condenses laser light at an object to be processed so as to form a modified region within the object along a line to cut. Therefore, the forming of the modified region will be explained at first with reference to FIGS. 1 to 6.

As illustrated in FIG. 1, a laser processing device 100 includes a laser light source 101 for causing laser light L to oscillate in a pulsating manner, a dichroic mirror 103 arranged to change a direction of the optical axis (optical path) of the laser light L by 90°, and a condensing lens 105 for condensing the laser light L. The laser processing device 100 further includes a support table 107 for supporting an object to be processed 1 which is irradiated with the laser light L condensed by the condensing lens 105, a stage 111 which is a moving mechanism for moving the support table 107, a laser light source controller 102 for controlling the laser light source 101 in order to adjust the output, pulse width, pulse waveform, and the like of the laser light L, and a stage controller 115 for controlling the movement of the stage 111.

In the laser processing device 100, the laser light L emitted from the laser light source 101 changes the direction of its optical axis by 90° with the dichroic mirror 103 and then is condensed by the condensing lens 105 at the object 1 mounted on the support table 107. At the same time, the stage 111 is shifted, so that the object 1 moves with respect to the laser light L along a line to cut 5. This forms a modified region in the object 1 along the line 5. While the stage 111 is shifted here for relatively moving the laser light L, the condensing lens 105 may be shifted instead or together therewith.

Figure 2:
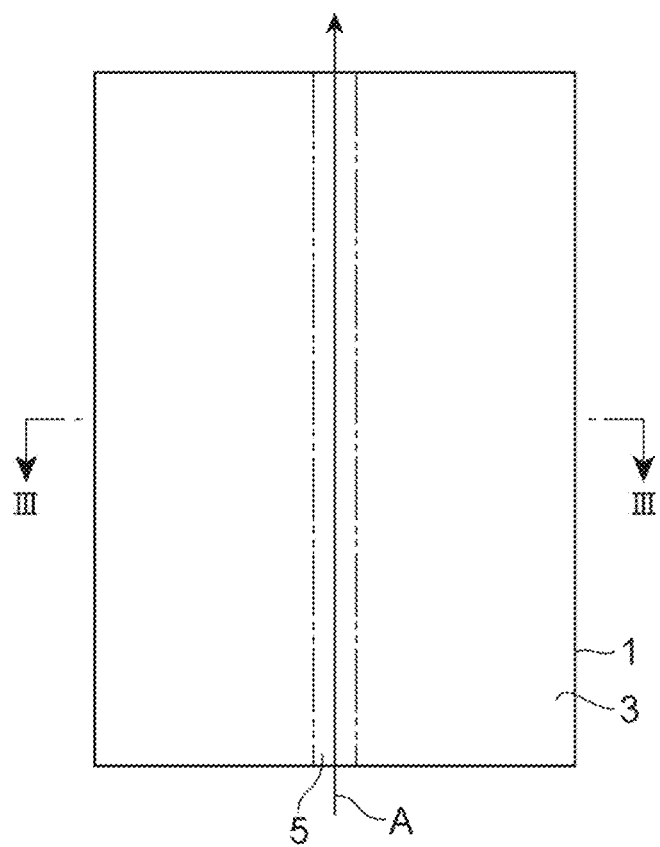
FIG. 2 is a plan view of an object to be processed for which the modified region is formed.
Figure 3:
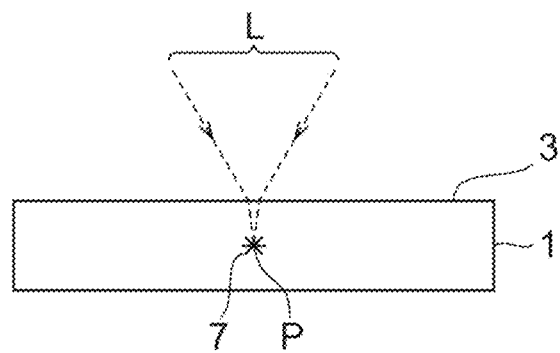
FIG. 3 is a sectional view of the object taken along the line of FIG. 2.
Figure 4:
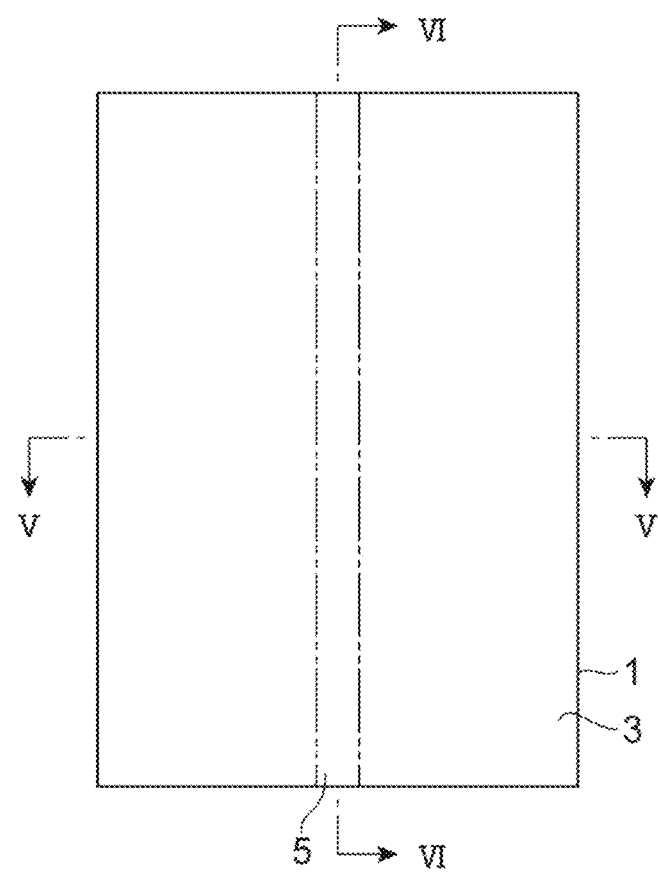
FIG. 4 is a plan view of the object after laser processing.
Figure 5:
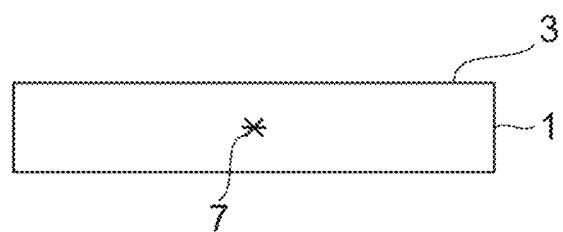
FIG. 5 is a sectional view of the object taken along the line V-V of FIG. 4.
Figure 6:
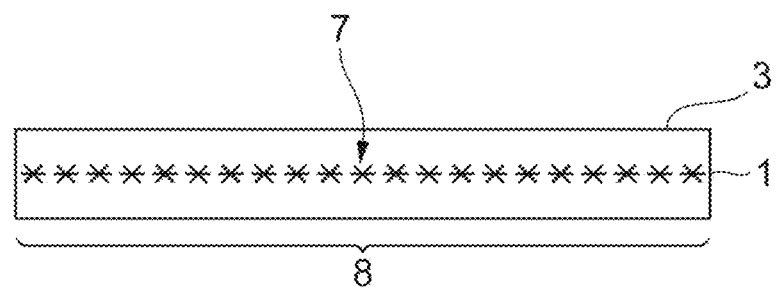
FIG. 6 is a sectional view of the object taken along the line VI-VI of FIG. 4.

Employed as the object 1 is a planar member (e.g., a substrate or a wafer), examples of which include semiconductor substrates formed of semiconductor materials and piezoelectric substrates formed of piezoelectric materials. As illustrated in FIG. 2, in the object 1, the line 5 is set for cutting the object 1. The line 5 is a virtual line extending straight. When forming a modified region within the object 1, the laser light L is relatively moved along the line 5 (i.e., in the direction of arrow A in FIG. 2) while locating a condensing point (condensing position) P within the object 1 as illustrated in FIG. 3. This forms a modified region 7 within the object 1 along the line 5 as illustrated in FIG. 4, FIG. 5 and FIG. 6, and whereby the modified region 7 formed along the line 5 becomes a cutting start region 8. The line 5 corresponds to a line to be irradiated.

The condensing point P is a position at which the laser light L is condensed. The line 5 may be curved instead of being straight, a three-dimensional one combining them, or one specified by coordinates. The line 5 may be one actually drawn on a front face 3 of the object 1 without being restricted to the virtual line. The modified region 7 may be formed either continuously or intermittently. The modified region 7 may be formed either in rows or dots and is only required to be formed at least the inside, the front face 3, or the rear face of the object 1. There are cases where fractures are formed from the modified region 7 acting as a start point, and the fractures and modified region 7 may be exposed at outer surfaces (the front face 3, rear face, and outer peripheral surface) of the object 1. The laser light entrance surface for forming the modified region 7 is not limited to the front face 3 of the object 1 but may be the rear face of the object 1.

Here, when the modified region 7 is formed within the object 1, the laser light L is absorbed in particular in the vicinity of the condensing point P within the object 1 while being transmitted therethrough. Therefore, the modified region 7 is formed in the object 1 (i.e., internal absorption type laser processing). In this case, the front face 3 of the object 1 hardly absorbs the laser light L and thus does not melt. On the other hand, when the modified region 7 is formed on the front face 3 or the rear face of the object 1, the laser light L is absorbed in particular in the vicinity of the condensing point P positioned on the front face 3 or the rear face and a removing part such as a hole or groove is formed by being molten and removed from the front face 3 or the rear face (surface absorption type laser processing).

The modified region 7 is a region of which physical characteristics such as density, refractive index, and mechanical strength have attained states different from those of their surroundings. Examples of the modified region 7 include molten processed regions (meaning at least one of regions resolidified after having been once molten, those in the molten state, and those in the process of resolidifying from the molten state), crack regions, dielectric breakdown regions, refractive index changed regions, and their mixed regions. Other examples of the modified region 7 include areas where the density of the modified region 7 has changed from that of an unmodified region and areas formed with a lattice defect in a material of the object 1. When the material of the object 1 is monocrystalline silicon, the modified region 7 can also be said to be a high dislocation density region.

The molten processed regions, refractive index changed regions, areas where the modified region 7 has a density different from that of the unmodified region, or areas formed with a lattice defect may further incorporate a fracture (cut or microcrack) therewithin or at an interface between the modified region 7 and the unmodified region. The incorporated fracture may be formed over the whole surface of the modified region 7 or in only a part or a plurality of parts thereof. The object 1 includes a substrate made of a crystal material having a crystal structure. Examples of the object 1 include a substrate made of at least one of gallium nitride (GaN), silicon (Si), silicon carbide (SiC), $LiTaO_3$, and sapphire ($Al_2O_3$). In other words, the object 1 includes, for example, a gallium nitride substrate, a silicon substrate, a SiC substrate, a $LiTaO_3$ substrate, or a sapphire substrate. The crystal material may be one of an anisotropic crystal and an isotropic crystal. In addition, the object 1 may include a substrate made of an amorphous material having a non-crystalline structure (amorphous structure) and may include, for example, a glass substrate.

This embodiment forms a plurality of modified spots (processing scars) along the line 5, thereby producing the modified region 7. In this case, the plurality of modified spots gather to yield the modified region 7. The modified spots is a modified part formed by a shot of one pulse of pulsed laser light (i.e., one pulse of laser irradiation; laser shot). Examples of the modified spots include crack spots, molten processed spots, refractive index changed spots, and those in which at least one of them is mixed. As for the modified spots, their size and lengths of fractures occurring therefrom can be controlled as necessary in view of the required cutting accuracy, the demanded flatness of cut surfaces, the thickness, kind, and crystal orientation of the object 1, and the like. In addition, in this embodiment, the modified spots can be formed as the modified region 7 along the line 5.

[Laser Processing Device According to Embodiment]

Next, the laser processing device according to this embodiment will be described. In the following description, the directions orthogonal to each other in the horizontal plane are defined as the X axis direction and the Y axis direction, and the vertical direction is defined as the Z axis direction.

[Overall Configuration of Laser Processing Device]

Figure 7:
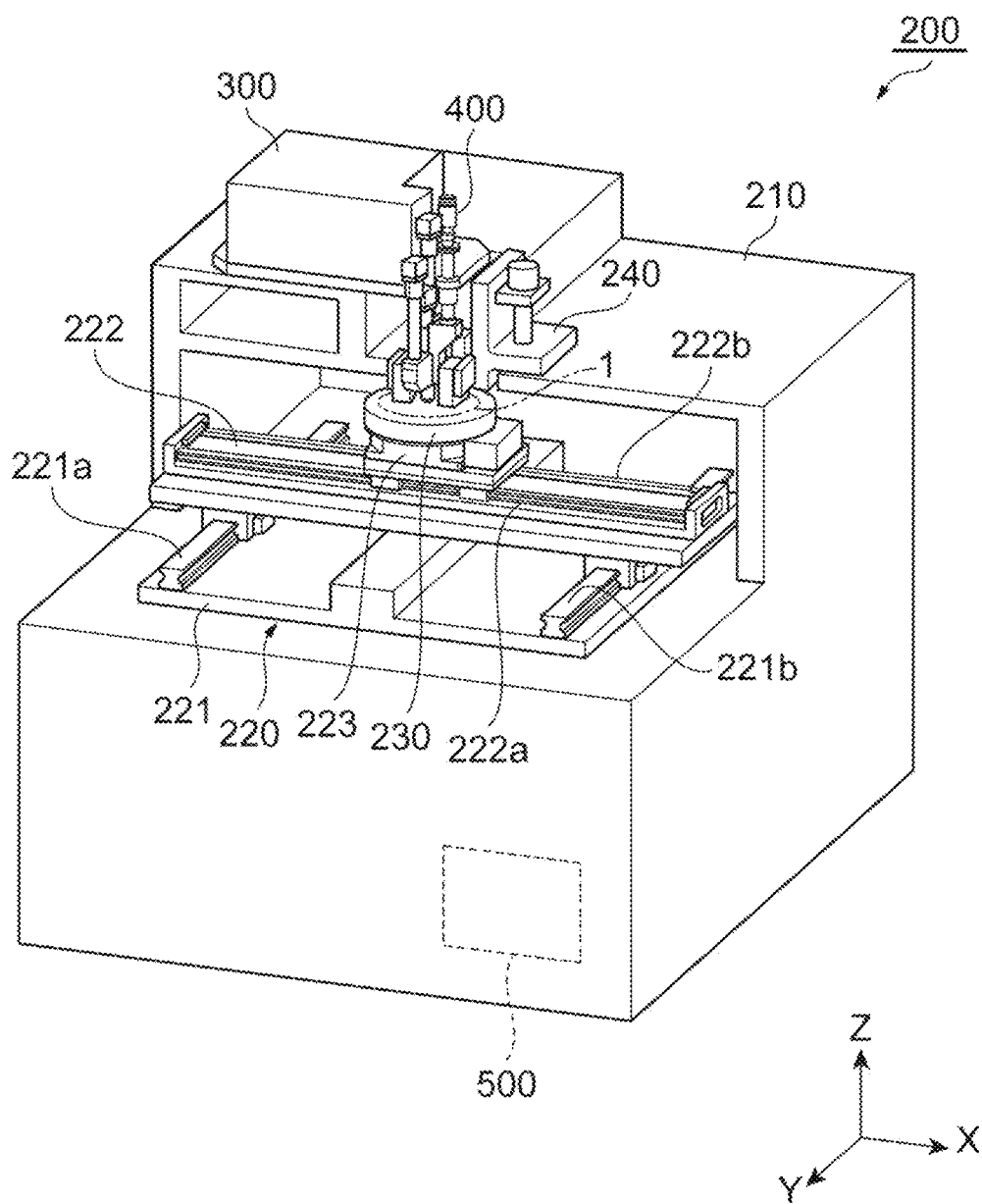
FIG. 7 is a perspective view of a laser processing device according to an embodiment.

As illustrated in FIG. 7, the laser processing device 200 includes a device frame 210, a first moving mechanism 220, a support table 230, and a second moving mechanism (moving mechanism) 240. Further, the laser processing device 200 includes a laser output unit 300, a laser condensing unit 400, and a controller 500.

The first moving mechanism 220 is attached to the device frame 210. The first moving mechanism 220 includes a first rail unit 221, a second rail unit 222, and a movable base 223. The first rail unit 221 is attached to the device frame 210. The first rail unit 221 is provided with a pair of rails 221a and 221b extending along the Y-axis direction. The second rail unit 222 is attached to the pair of rails 221a and 221b of the first rail unit 221 so as to be movable along the Y-axis direction. The second rail unit 222 is provided with a pair of rails 222a and 222b extending along the X-axis direction. The movable base 223 is attached to the pair of rails 222a and 222b of the second rail unit 222 so as to be movable along the X-axis direction. The movable base 223 is rotatable about the axis parallel to the Z-axis direction as the center line.

Figure 8:
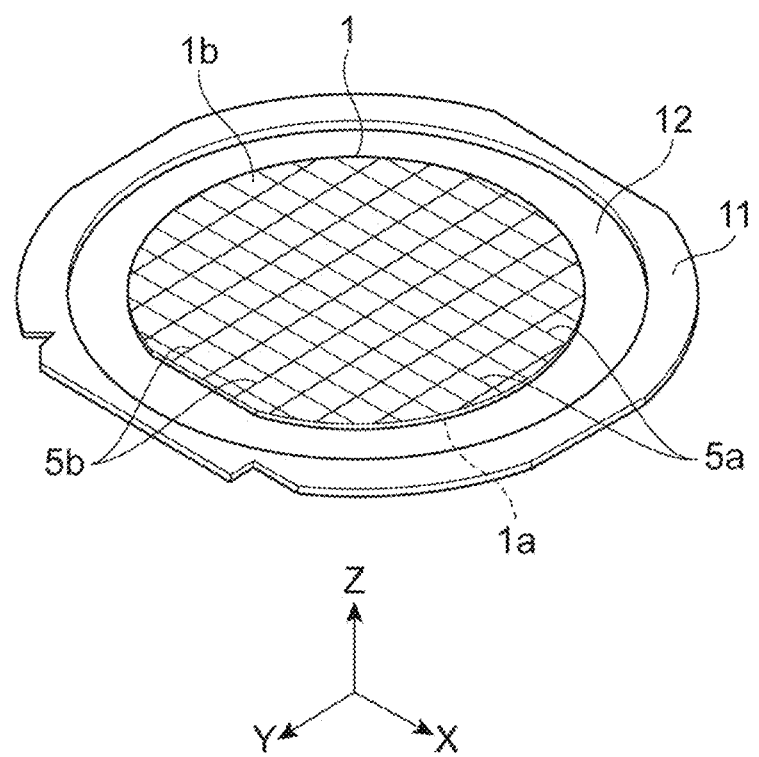
FIG. 8 is a perspective view of an object to be processed, which is attached to a support table of the laser processing device of FIG. 7.

The support table 230 is attached to the movable base 223. The support table 230 supports the object 1. The object 1 is a plurality of functional elements (a light receiving element such as a photodiode, a light emitting element such as a laser diode, or a circuit element formed as a circuit, or the like) formed on a front face of a substrate made of a semiconductor material such as silicon in a matrix shape, for example. When the object 1 is supported on the support table 230, as illustrated in FIG. 8, for example, the front face a (the surface on the plurality of functional element sides) of the object 1 is attached onto the film 12 stretched over the annular frame 11. The support table 230 supports the object 1 by holding the frame 11 by clamping and adsorbing the film 12 with a vacuum chuck table. On the support table 230, a plurality of mutually parallel lines 5a and a plurality of mutually parallel lines 5b are set to the object 1 in a grid shape so as to pass between adjacent functional elements. The object 1 has a plate shape of a predetermined thickness (here, 775 μm). The predetermined thickness of the object 1 is not limited, and various thicknesses are also acceptable.

As illustrated in FIG. 7, when the second rail unit 222 is operated in the first moving mechanism 220, the support table 230 is moved along the Y-axis direction. In addition, when the movable base 223 is operated in the first moving mechanism 220, the support table 230 is moved along the X-axis direction. Furthermore, when the movable base 223 is operated in the first moving mechanism 220, the support table 230 is rotated about the axis parallel to the Z-axis direction as the center line. In this manner, the support table 230 is attached to the device frame 210 so as to be movable along the X-axis direction and the Y-axis direction and to be rotatable about the axis parallel to the Z-axis direction as the center line.

The laser output unit 300 is attached to the device frame 210. The laser condensing unit 400 is attached to the device frame 210 through the second moving mechanism 240. The laser condensing unit 400 is moved along the Z-axis direction by the operation of the second moving mechanism 240. In this manner, the laser condensing unit 400 is attached to the device frame 210 so as to be movable along the Z-axis direction with respect to the laser output unit 300.

The controller 500 includes a central processing unit (CPU), a read only memory (ROM), a random access memory (RAM), and the like. The controller 500 controls the operation of each unit of the laser processing device 200.

As an example, in the laser processing device 200, the modified region is formed inside the object 1 along each of the lines 5a and 5b (see FIG. 8) as follows.

First, the object 1 is supported on the support table 230 so that the rear face 1b of the object 1 (see FIG. 8) becomes the laser light entrance surface, and each line 5a of the object 1 is aligned with the X-axis direction. Subsequently, the laser condensing unit 400 is moved by the second moving mechanism 240 such that the condensing point of the laser beam L is positioned at a position separated from the laser light entrance surface of the object 1 by a predetermined distance inside the object 1. Subsequently, while the distance between the laser light entrance surface of the object 1 and the condensing point of the laser beam L is maintained constant, the condensing point of the laser beam L relatively moves along each of the line 5a. Therefore, the modified region is formed inside the object 1 along each line 5a.

When the formation of the modified region along line 5a is completed, the support table 230 is rotated by the first moving mechanism 220, and each line 5b of the object 1 moves in the direction parallel to the X-axis direction. Subsequently, the laser condensing unit 400 is moved by the second moving mechanism 240 such that the condensing point of the laser beam L is positioned at a position separated from the laser light entrance surface of the object 1 by a predetermined distance inside the object 1. Subsequently, while the distance between the laser light entrance surface of the object 1 and the condensing point of the laser beam L is maintained constant, the condensing point of the laser beam L relatively moves along each of the line 5b. Therefore, the modified region is formed inside the object 1 along each line 5b.

As described above, in the laser processing device 200, the direction parallel to the X-axis direction is the processing direction (the scanning direction of the laser light L). The relative movement of the condensing point of the laser light L along each line 5a and the relative movement of the condensing point of the laser beam L along each line 5b are carried out by moving the support table 230 along the X-axis direction by the first moving mechanism 220. The relative movement of the condensing point of the laser beam L between the respective lines 5a and the relative movement of the condensing point of the laser beam L between the respective lines 5b are carried out by moving the support table 230 along the Y-axis direction by the first moving mechanism 220.

Figure 9:
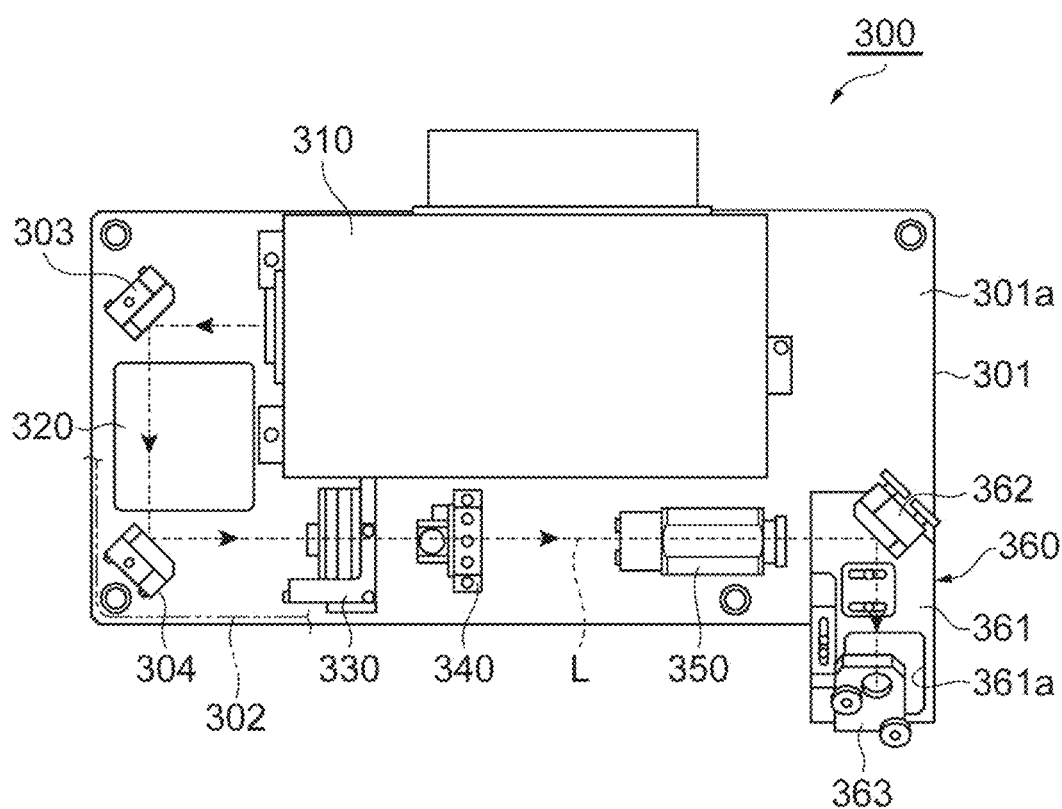
FIG. 9 is a sectional view of a laser output unit taken along the ZX plane of FIG. 7.

As illustrated in FIG. 9, the laser output unit 300 includes a mounting base 301, a cover 302, and a plurality of mirrors 303 and 304. Further, the laser output unit 300 includes a laser oscillator (laser light source) 310, a shutter 320, a λ/2 wave plate unit 330, a polarizing plate unit 340, a beam expander 350, and a mirror unit 360.

The mounting base 301 supports the plurality of mirrors 303 and 304, the laser oscillator 310, the shutter 320, the λ/2 wave plate unit 330, the polarizing plate unit 340, the beam expander 350, and the mirror unit 360. The plurality of mirrors 303 and 304, the laser oscillator 310, the shutter 320, the λ/2 wave plate unit 330, the polarizing plate unit 340, the beam expander 350, and the mirror unit 360 are attached to a main surface 301a of the mounting base 301. The mounting base 301 is a plate-like member and is attachable to and detachable from the device frame 210 (see FIG. 7). The laser output unit 300 is attached to the device frame 210 through the mounting base 301. That is, the laser output unit 300 is attachable to and detachable from the device frame 210.

The cover 302 covers the plurality of mirrors 303 and 304, the laser oscillator 310, the shutter 320, the λ/2 wave plate unit 330, the polarizing plate unit 340, the beam expander 350, and the mirror unit 360 on the main surface 301a of the mounting base 301. The cover 302 is attachable to and detachable from the mounting base 301.

The laser oscillator 310 oscillates linearly polarized laser light L in a pulsating manner along the X-axis direction. A wavelength of the laser light L emitted from the laser oscillator 310 is included in a wavelength band of 500 nm to 550 nm, 1000 run to 1150 nm, or 1300 nm to 1400 nm. The laser light L in the wavelength band of 500 nm to 550 nm is suitable for internal absorption type laser processing on the substrate made of, for example, sapphire. The laser light L in the wavelength bands of 1000 nm to 1150 nm and 1300 nm to 1400 nm is suitable for internal absorption type laser processing on the substrate made of, for example, silicon. A polarization direction of the laser light L emitted from the laser oscillator 310 is, for example, a direction parallel to the Y-axis direction. The laser beam L emitted from the laser oscillator 310 is reflected by the mirror 303 and is incident on the shutter 320 along the Y-axis direction.

In the laser oscillator 310, ON/OFF of the output of the laser light L is switched as follows. When the laser oscillator 310 is constituted by a solid state laser, ON/OFF of a Q switch (an acousto-optic modulator (AOM), an electro-optic modulator (EOM), or the like) provided in a resonator is switched so that ON/OFF of the output of the laser light L is switched at high speed. When the laser oscillator 310 is constituted by a fiber laser, ON/OFF of the output of a semiconductor laser constituting a seed laser and an amplifier (excitation) laser is switched so that ON/OFF of the output of the laser light L is switched at high speed. When the laser oscillator 310 uses an external modulation element, ON/OFF of an external modulation element (AOM, EOM, or the like) provided outside the resonator is switched so that ON/OFF of the output of the laser light L is switched at high speed.

The shutter 320 opens and closes the optical path of the laser light L by a mechanical mechanism. The ON/OFF switching of the output of the laser light L from the laser output unit 300 is performed by the ON/OFF switching of the output of the laser light L in the laser oscillator 310 as described above. Since the shutter 320 is provided, for example, unexpected emission of the laser light L from the laser output unit 300 is prevented. The laser light L that has passed through the shutter 320 is reflected by the mirror 304 and is sequentially incident on the λ/2 wave plate unit 330 and the polarizing plate unit 340 along the X-axis direction.

The λ/2 wave plate unit 330 and the polarizing plate unit 340 function as an output adjustment unit for adjusting the output (light intensity) of the laser light L. In addition, the λ/2 wave plate unit 330 and the polarizing plate unit 340 function as a polarization direction adjustment unit for adjusting the polarization direction of the laser light L. The laser light L having sequentially passed through the λ/2 wave plate unit 330 and the polarizing plate unit 340 is incident on the beam expander 350 along the X-axis direction.

The beam expander 350 collimates the laser light L while adjusting the diameter of the laser light L. The laser light L having passed through the beam expander 350 is incident on the mirror unit 360 along the X-axis direction.

The mirror unit 360 includes a support base 361 and a plurality of mirrors 362 and 363. The support base 361 supports the plurality of mirrors 362 and 363. The support base 361 is attached to the mounting base 301 so that the position can be adjusted along the X-axis direction and the Y-axis direction. The mirror (first mirror) 362 reflects the laser light L that has passed through the beam expander 350 in the Y-axis direction. The mirror 362 is attached to the support base 361 such that the reflection surface thereof is adjustable in angle about, for example, the axis parallel to the Z axis. The mirror (second mirror) 363 reflects the laser light L reflected by the mirror 362 in the Z-axis direction. The mirror 363 is attached to the support base 361 such that the reflection surface thereof can be adjusted in angle about, for example, the axis parallel to the X axis and can be adjusted in position along the Y-axis direction. The laser light L reflected by the mirror 363 passes through an opening 361a formed in the support base 361 and is incident on the laser condensing unit 400 along the Z-axis direction (see FIG. 7). In other words, the emission direction of the laser light L by the laser output unit 300 coincides with the movement direction of the laser condensing unit 400. As described above, each of the mirrors 362 and 363 has a mechanism for adjusting the angle of the reflection surface. The position adjustment of the support base 361 with respect to the mounting base 301, the position adjustment of the mirror 363 with respect to the support base 361, and the angle adjustment of the reflection surfaces of the mirrors 362 and 363 are performed in the mirror unit 360 such that the position and the angle of the optical axis of the laser light L emitted from the laser output unit 300 are matched with respect to the laser condensing unit 400. That is, the plurality of mirrors 362 and 363 are configured to adjust the optical axis of the laser light L emitted from the laser output unit 300.

Figure 10:
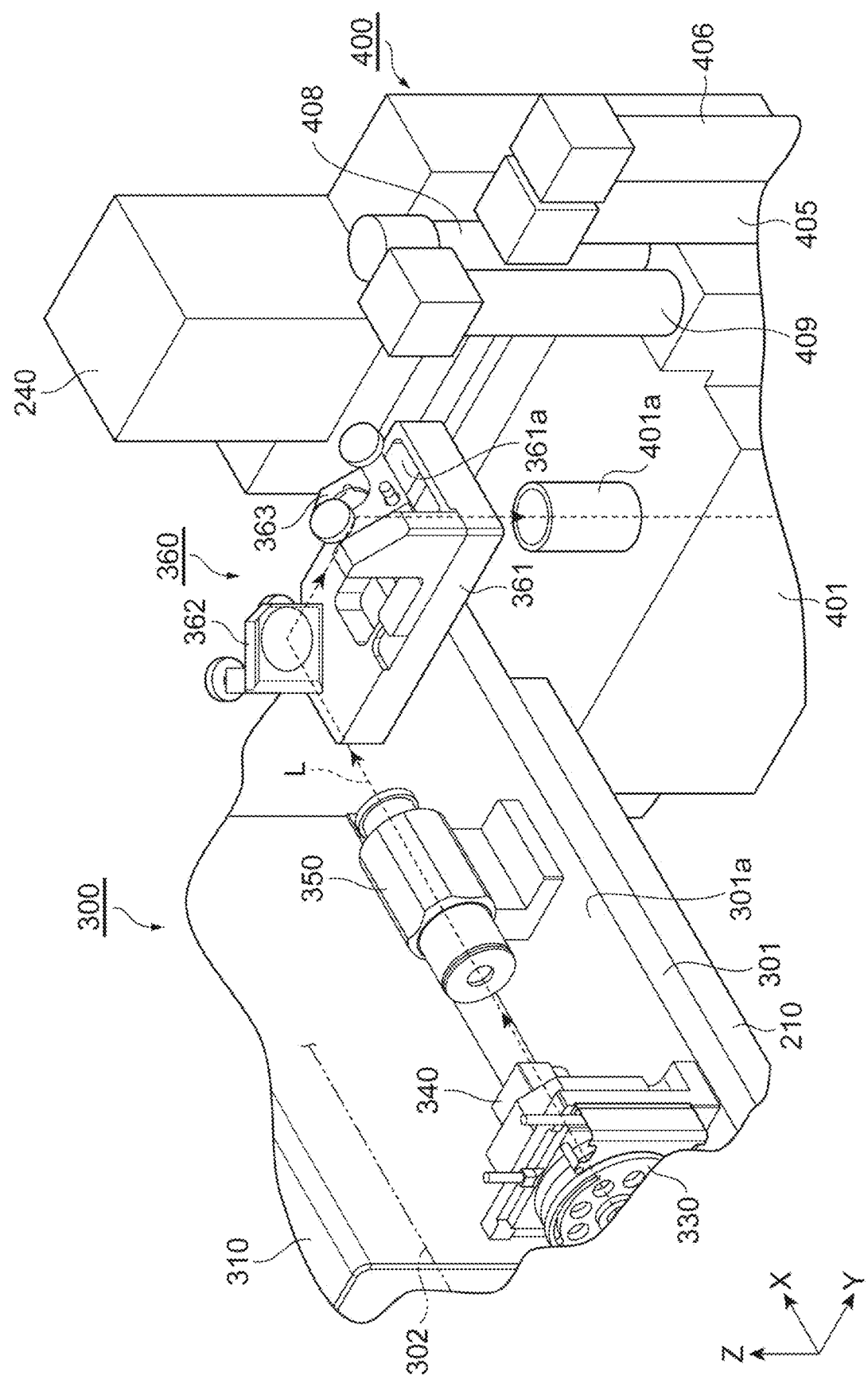
FIG. 10 is a perspective view of a part of a laser output unit and a laser condensing unit in the laser processing device of FIG. 7.

As illustrated in FIG. 10, the laser condensing unit 400 includes a housing 401. The housing 401 has a rectangular parallelepiped shape with the Y-axis direction as the longitudinal direction. The second moving mechanism 240 is attached to one side face 401e of the housing 401 (see FIGS. 11 and 13). A cylindrical light entrance part 401a is provided in the housing 401 so as to face the opening 361a of the mirror unit 360 in the Z-axis direction. The light entrance part 401a allows the laser light L emitted from the laser, output unit 300 to enter the inside of the housing 401. The mirror unit 360 and the light entrance part 401a are separated from each other by a distance that does not contact each other when the laser condensing unit 400 is moved along the Z-axis direction by the second moving mechanism 240.

Figure 11:
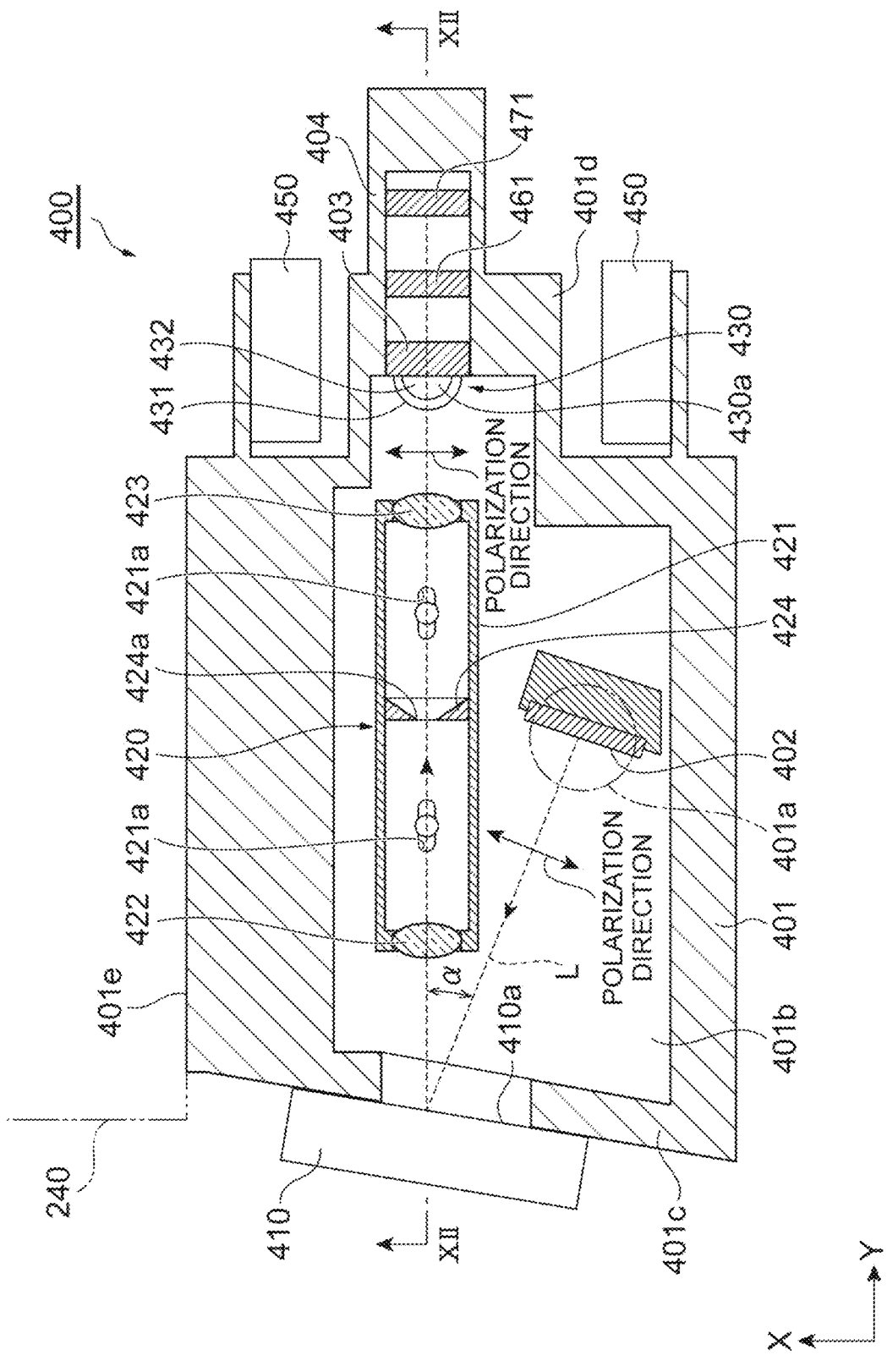
FIG. 11 is a sectional view of the laser condensing unit taken along the XY plane of FIG. 7.
Figure 12:
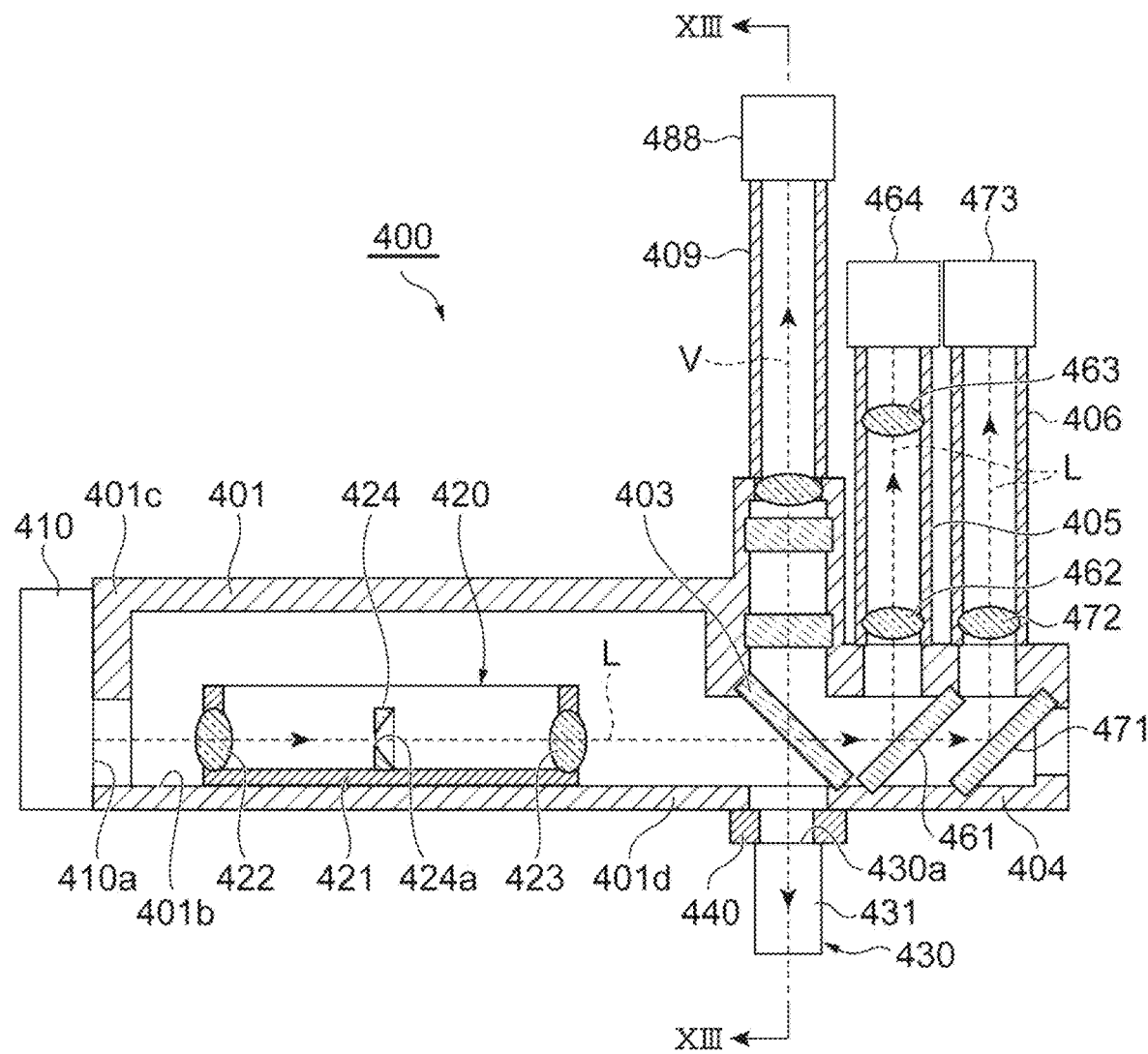
FIG. 12 is a sectional view of the laser condensing unit taken along the line XII-XII of FIG. 11.

As illustrated in FIGS. 11 and 12, the laser condensing unit 400 includes a mirror 402 and a dichroic mirror 403. Further, the laser condensing unit 400 includes a reflective spatial light modulator 410, a 4f lens unit 420, a condensing lens unit (objective lens) 430, a driving mechanism 440, and a pair of distance measurement sensors 450.

The mirror 402 is attached to a bottom face 401b of the housing 401 so as to face the light entrance part 401a in the Z-axis direction. The mirror 402 reflects the laser light L entering the housing 401 through the light entrance part 401a in a direction parallel to the XY plane. The laser light L collimated by the beam expander 350 of the laser output unit 300 is incident on the mirror 402 along the Z-axis direction. That is, the laser light L is incident on the mirror 402 as parallel light along the Z-axis direction. Therefore, even if the laser condensing unit 400 is moved along the Z-axis direction by the second moving mechanism 240, the state of the laser light L incident on the mirror 402 along the Z-axis direction is maintained constant. The laser light L reflected by the mirror 402 is incident on the reflective spatial light modulator 410.

The reflective spatial light modulator 410 is attached to an end portion 401c of the housing 401 in the Y-axis direction in a state in which a reflection surface 410a faces the inside of the housing 401. The reflective spatial light modulator 410 is, for example, a reflective liquid crystal (liquid crystal on silicon (LCOS)) spatial light modulator (SLM) and reflects the laser light L in the Y-axis direction while modulating the laser light L. The laser light L modulated and reflected by the reflective spatial light modulator 410 is incident on the 4f lens unit 420 along the Y-axis direction. Here, in the plane parallel to the XY plane, the angle α formed between the optical axis of the laser light L incident on the reflective spatial light modulator 410 and the optical axis of the laser light L emitted from the reflective spatial light modulator 410 is an acute angle (for example, 10° to 60°). That is, the laser light L is reflected at an acute angle along the XY plane in the reflective spatial light modulator 410. This is because the reduction in the diffraction efficiency is suppressed by suppressing the incident angle and the reflection angle of the laser light L, and the performance of the reflective spatial light modulator 410 is sufficiently exhibited. In the reflective spatial light modulator 410, for example, since the thickness of the light modulation layer in which the liquid crystal is used is as thin as about several μm to several tens μm, the reflection surface 410a can be regarded as substantially the same as the light entrance/exit surface of the light modulation layer.

The 4f lens unit 420 includes a holder 421, a lens 422 on the reflective spatial light modulator 410 side, a lens 423 on the condensing lens unit 430 side, and a slit member 424. The holder 421 holds the pair of lenses 422 and 423 and the slit member 424. The holder 421 maintains a positional relationship between the pair of lenses 422 and 423 and the slit member 424 constant in the direction along the optical axis of the laser light L. The pair of lenses 422 and 423 constitute a double-telecentric optical system in which the reflection surface 410a of the reflective spatial light modulator 410 and the entrance pupil plane (pupil plane) 430a of the condensing lens unit 430 are in an image-forming relationship. In this manner, the image of the laser light L on the reflection surface 410a of the reflective spatial light modulator 410 (the image of the laser light L modulated in the reflective spatial light modulator 410) is transferred (imaged) onto the entrance pupil plane 430a of the condensing lens unit 430. A slit 424a is foisted in the slit member 424. The slit 424a is positioned between the lens 422 and the lens 423 and is positioned near the condensing plane of the lens 422. An unnecessary part of the laser light L modulated and reflected by the reflective spatial light modulator 410 is blocked by the slit member 424. The laser light L having passed through the 4f lens unit 420 is incident on the dichroic mirror 403 along the Y-axis direction.

The dichroic mirror 403 reflects a major part (for example, 95% to 99.5%) of the laser light L in the Z-axis direction and a part (for example, 0.5% to 5%) of the laser light L along the Y-axis direction. Most of the laser light L is reflected at right angle along the ZX plane in the dichroic mirror 403. The laser light L reflected by the dichroic mirror 403 is incident on the condensing lens unit 430 along the Z-axis direction.

The condensing lens unit 430 is attached to an end portion 401d (an end portion on the side opposite to the end portion 401c) of the housing 401 in the Y-axis direction through the driving mechanism 440. The condensing lens unit 430 includes a holder 431 and a plurality of lenses 432. The holder 431 holds the plurality of lenses 432. The plurality of lenses 432 condense the laser light L to the object 1 supported by the support table 230 (see FIG. 7). The driving mechanism 440 moves the condensing lens unit 430 along the Z-axis direction by a driving force of a piezoelectric element.

The pair of distance measurement sensors 450 are attached to the end portion 401d of the housing 401 so as to be positioned on both sides of the condensing lens unit 430 in the X-axis direction. Each of the distance measurement sensors 450 acquires displacement data of the laser light entrance surface of the object 1 by emitting distance measurement light (for example, laser light) to the laser light entrance surface of the object 1 supported by the support table 230 (see FIG. 7) and detecting the distance measurement light reflected by the laser light entrance surface. The distance measurement sensor 450 can use a sensor of a triangulation method, a laser confocal method, a white confocal method, a spectral interference method, an astigmatism method, or the like.

As described above, in the laser processing device 200, the direction parallel to the X-axis direction is the processing direction (the scanning direction of the laser light L). Therefore, when the condensing point of the laser light L is relatively moved along each of the lines 5a and 5b, the distance measurement sensor 450 relatively preceding the condensing lens unit 430 among the pair of distance measurement sensors 450 acquires displacement data of the laser light entrance surface of the object 1 along each of the lines 5a and 5h. The driving mechanism 440 moves the condensing lens unit 430 along the Z-axis direction based on the displacement data acquired by the distance measurement sensor 450, such that the distance between the laser light entrance surface of the object 1 and the condensing point of the laser light L is maintained constant.

The laser condensing unit 400 includes a beam splitter 461, a pair of lenses 462 and 463, and a profile acquisition camera 464. The beam splitter 461 divides the laser light L transmitted through the dichroic mirror 403 into a reflective component and a transmissive component. The laser light L reflected by the beam splitter 461 is sequentially incident on the pair of lenses 462 and 463 and the profile acquisition camera 464 along the Z-axis direction. The pair of lenses 462 and 463 constitute a double-telecentric optical system in which the entrance pupil plane 430a of the condensing lens unit 430 and the imaging plane of the profile acquisition camera 464 are in an image-forming relationship. Therefore, the image of the laser light L on the entrance pupil plane 430a of the condensing lens unit 430 is transferred (imaged) onto the imaging plane of the profile acquisition camera 464. As described above, the image of the laser light L on the entrance pupil plane 430a of the condensing lens unit 430 is the image of the laser light L modulated in the reflective spatial light modulator 410. Therefore, in the laser processing device 200, it is possible to grasp the operation state of the reflective spatial light modulator 410 by monitoring the imaging result by the profile acquisition camera 464.

Further, the laser condensing unit 400 includes a beam splitter 471, a lens 472, and a camera 473 for monitoring the optical axis position of the laser light L. The beam splitter 471 divides the laser light L transmitted through the beam splitter 461 into a reflective component and a transmissive component. The laser beam L reflected by the beam splitter 471 is sequentially incident on the lens 472 and the camera 473 along the Z-axis direction. The lens 472 condenses the incident laser light L on the imaging surface of the camera 473. In the laser processing device 200, while monitoring the imaging results by the profile acquisition camera 464 and the camera 473, the shift of the optical axis of the laser light L incident on the condensing lens unit 430 (the positional shift of the intensity distribution of the laser light with respect to the condensing lens unit 430 and the angular shift of the optical axis of the laser light L with respect to the condensing lens unit 430) can be corrected by adjusting the position of the support base 361 with respect to the mounting base 301, adjusting the position of the mirror 363 with respect to the support base 361, and adjusting the angle of the reflection surfaces of the mirrors 362 and 363 in the mirror unit 360 (see FIGS. 9 and 10), The plurality of beam splitters 461 and 471 are disposed in a cylindrical body 404 extending from the end portion 401d of the housing 401 along the Y-axis direction. The pair of lenses 462 and 463 are disposed in a cylindrical body 405 erected on the cylindrical body 404 along the Z-axis direction, and the profile acquisition camera 464 is disposed at an end portion of the cylindrical body 405. The lens 472 is disposed in a cylindrical body 406 erected on the cylindrical body 404 along the Z-axis direction, and the camera 473 is disposed at an end portion of the cylindrical body 406. The cylindrical body 405 and the cylindrical body 406 are juxtaposed to each other in the Y-axis direction.

The laser light L transmitted through the beam splitter 471 may be absorbed by a damper or the like provided at an end portion of the cylindrical body 404, or may be used for appropriate purposes.

Figure 13:
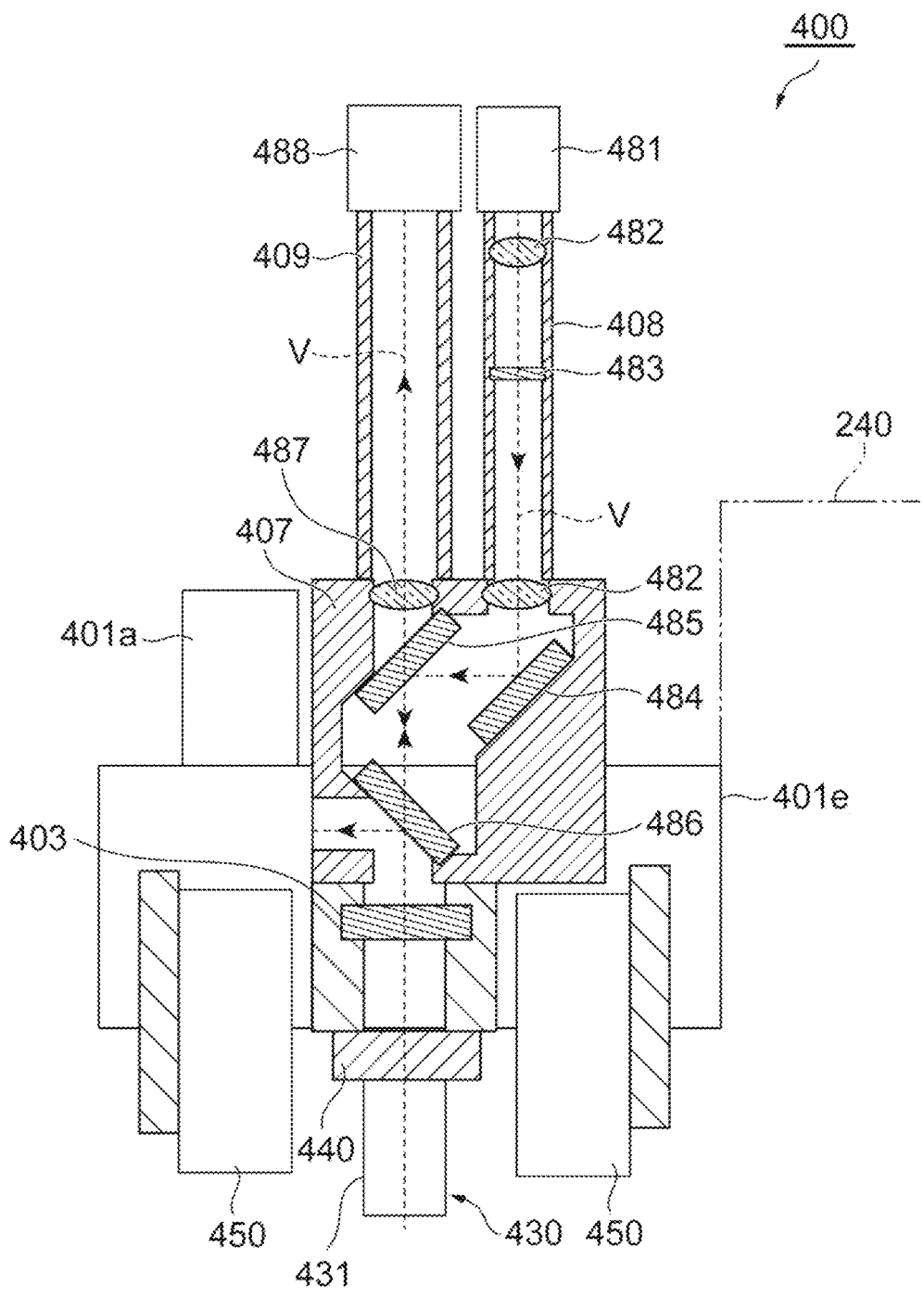
FIG. 13 is a sectional view of the laser condensing unit taken along the line XIII-XIII of FIG. 12.

As illustrated in FIGS. 12 and 13, the laser condensing unit 400 includes a visible light source 481, a plurality of lenses 482, a reticle 483, a mirror 484, a half mirror 485, a beam splitter 486, a lens 487, and an observation camera 488. The visible light source 481 emits visible light V along the Z-axis direction. The plurality of lenses 482 collimate the visible light V emitted from the visible light source 481. The reticle 483 gives a graduation line to the visible light V. The mirror 484 reflects the visible light V collimated by the plurality of lenses 482 in the X-axis direction. The half mirror 485 divides the visible light V reflected by the mirror 484 into a reflective component and a transmissive component. The visible light V reflected by the half mirror 485 sequentially passes through the beam splitter 486 and the dichroic mirror 403 along the Z-axis direction and is irradiated onto the object 1 (see FIG. 7) supported by the support table 230 through the condensing lens unit 430.

The visible light V irradiated onto the object 1 is reflected by the laser light entrance surface of the object 1, is incident on the dichroic mirror 403 through the condensing lens unit 430, and passes through the dichroic mirror 403 along the Z-axis direction. The beam splitter 486 divides the visible light V transmitted through the dichroic mirror 403 into a reflective component and a transmissive component. The visible light V transmitted through the beam splitter 486 transmits through the half mirror 485 and is sequentially incident on the lens 487 and the observation camera 488 along the Z-axis direction. The lens 487 condenses the incident visible light V on the imaging surface of the observation camera 488. In the laser processing device 200, it is possible to grasp the state of the object 1 by observing the imaging result by the observation camera 488.

The mirror 484, the half mirror 485, and the beam splitter 486 are disposed in a holder 407 attached on the end portion 401d of the housing 401. The plurality of lenses 482 and the reticle 483 are disposed in a cylindrical body 408 erected on the holder 407 along the Z-axis direction, and the visible light source 481 is disposed at an end portion of a cylindrical body 408. The lens 487 is disposed in a cylindrical body 409 erected on the holder 407 along the Z-axis direction, and the observation camera 488 is disposed at an end portion of a cylindrical body 409. The cylindrical body 408 and the cylindrical body 409 are juxtaposed to each other in the X-axis direction. The visible light V transmitted through the half mirror 485 along the X-axis direction and the visible light V reflected in the X-axis direction by the beam splitter 486 may be absorbed by a damper or the like provided on a wall portion of the holder 407, or may be used for appropriate purposes.

In the laser processing device 200, replacement of the laser output unit 300 is assumed. This is because the wavelength of the laser light L suitable for processing varies depending on the specification of the object 1, processing conditions, and the like. Therefore, a plurality of laser output units 300 having different wavelengths of emitted laser light L are prepared. Here, the laser output unit 300 in which the wavelength of the emitted laser light L is included in a wavelength band of 500 nm to 550 nm, the laser output unit 300 in which the wavelength of the emitted laser light L is included in a wavelength band of 1000 nm to 1150 nm, the laser output unit 300 in which the wavelength of the emitted laser light L is included in a wavelength band of 1300 nm to 1400 nm are prepared.

On the other hand, in the laser processing device 200, replacement of the laser condensing unit 400 is not assumed. This is because the laser condensing unit 400 corresponds to multiple wavelengths (corresponding to a plurality of wavelength bands not continuous with each other). Specifically, the mirror 402, the reflective spatial light modulator 410, the pair of lenses 422 and 423 of the 4f lens unit 420, the dichroic mirror 403, the lens 432 of the condensing lens unit 430, and the like correspond to multiple wavelengths. Here, the laser condensing unit 400 corresponds to wavelength bands of 500 nm to 550 nm, 1000 nm to 1150 nm, and 1300 nm to 1400 nm. This is realized by designing each configuration of the laser condensing unit 400 so as to satisfy desired optical performance such as coating of a predetermined dielectric multilayer film on each configuration of the laser condensing unit 400. In the laser output unit 300, the λ/2 wave plate unit 330 includes a λ/2 wavelength plate, and the polarizing plate unit 340 includes a polarizing plate. The λ/2 wavelength plate and the polarizing plate are optical elements having high wavelength dependence. Therefore, the λ/2 wave plate unit 330 and the polarizing plate unit 340 are provided in the laser output unit 300 as different configurations for each wavelength band.

[Optical Path and Polarization Direction of Laser Light in Laser Processing Device]

In the laser processing device 200, as illustrated in FIG. 11, the polarization direction of the laser light L condensed at the object 1 supported by the support table 230 is a direction parallel to the X-axis direction and coincides with the processing direction (the scanning direction of the laser light L). Here, in the reflective spatial light modulator 410, the laser light L is reflected as P-polarized light. This is because in a case in which liquid crystal is used for the light modulation layer of the reflective spatial light modulator 410, when the liquid crystal is aligned such that the liquid crystal molecules are tilted in a plane parallel to the plane including the optical axis of the laser light L incident and emitted to and from the reflective spatial light modulator 410, phase modulation is performed on the laser light L in a state in which rotation of the polarization plane is suppressed (see, for example, Japanese Patent No. 3878758). On the other hand, in the dichroic mirror 403, the laser light L is reflected as S-polarized light. This is because it is easier to design the dichroic mirror 403 by reflecting the laser light L as S-polarized light rather than reflecting the laser light L as P-polarized light, such as reduction in the number of coatings of the dielectric multilayer film for making the dichroic mirror 403 correspond to multiple wavelengths.

Therefore, in the laser condensing unit 400, the optical path from the mirror 402 to the dichroic mirror 403 through the reflective spatial light modulator 410 and the 4f lens unit 420 is set along the XY plane, and the optical path from the dichroic mirror 403 to the condensing lens unit 430 is set along the Z-axis direction.

As illustrated in FIG. 9, in the laser output unit 300, the optical path of the laser light L is set along the X-axis direction or the Y-axis direction. Specifically, the optical path from the laser oscillator 310 to the mirror 303 and the optical path from the mirror 304 to the mirror unit 360 through the λ/2 wave plate unit 330, the polarizing plate unit 340, and the beam expander 350 are set along the X-axis direction, and the optical path from the mirror 303 to the mirror 304 through the shutter 320 and the optical path from the mirror 362 to the mirror 363 in the mirror unit 360 are set along the Y-axis direction.

Here, as illustrated in FIG. 11, the laser light L traveling from the laser output unit 300 to the laser condensing unit 400 along the Z-axis direction is reflected by the mirror 402 in a direction parallel to the XY plane and is incident on the reflective spatial light modulator 410. At this time, in the plane parallel to the XY plane, the optical axis of the laser light L incident on the reflective spatial light modulator 410 and the optical axis of the laser light L emitted from the reflective spatial light modulator 410 form an acute angle α. On the other hand, as described above, in the laser output unit 300, the optical path of the laser light L is set along the X-axis direction or the Y-axis direction.

Therefore, in the laser output unit 300, the λ/2 wave plate unit 330 and the polarizing plate unit 340 need to function not only as an output adjustment unit for adjusting the output of the laser light L but also as a polarization direction adjustment unit for adjusting the polarization direction of the laser light L.

[Reflective Spatial Light Modulator]

Figure 14:
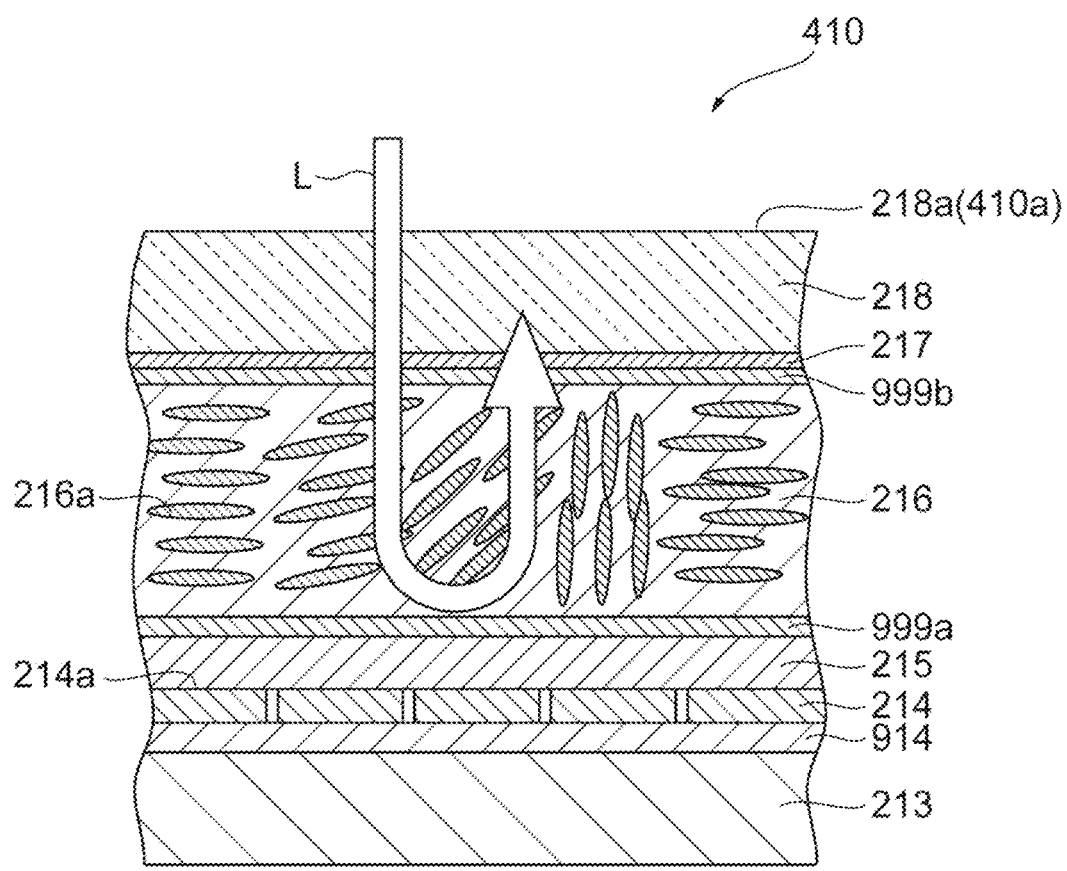
FIG. 14 is a partial sectional view of a reflective spatial light modulator in the laser processing device of FIG. 7.

As illustrated in FIG. 14, the reflective spatial light modulator 410 has a configuration in which a silicon substrate 213, a driving circuit layer 914, a plurality of pixel electrodes 214, a reflective film 215 such as a dielectric multilayer film mirror, an alignment film 999a, a liquid crystal layer (display portion) 216, an alignment film 999b, a transparent conductive film 217, and a transparent substrate 218 such as a glass substrate are stacked in this order.

The transparent substrate 218 has a front face 218a along the XY plane, and the front face 218a constitutes the reflection surface 410a of the reflective spatial light modulator 410. The transparent substrate 218 is made of a light transmissive material such as glass and transmits laser light L of a predetermined wavelength incident from the front face 218a of the reflective spatial light modulator 410 to the inside of the reflective spatial light modulator 410. The transparent conductive film 217 is formed on the rear face of the transparent substrate 218 and is made of a conductive material (for example, ITO) that transmits the laser light L.

The plurality of pixel electrodes 214 are arranged in a matrix form on the silicon substrate 213 along the transparent conductive film 217. Each pixel electrode 214 is made of, for example, a metal material such as aluminum and the front face 214a thereof is flat and smoothly processed. The plurality of pixel electrodes 214 are driven by an active matrix circuit provided in the driving circuit layer 914.

The active matrix circuit is provided between the plurality of pixel electrodes 214 and the silicon substrate 213 and controls a voltage applied to each pixel electrode 214 according to an optical image to be output from the reflective spatial light modulator 410. Such an active matrix circuit includes, for example, a first driver circuit for controlling an applied voltage of each pixel array arranged in the X-axis direction (not illustrated) and a second driver circuit for controlling an applied voltage of each pixel array arranged in the Y-axis direction, and is configured such that a predetermined voltage is applied to the pixel electrode 214 of the pixel designated by both the driver circuits by a spatial light modulator controller 502 (see FIG. 16) in a controller 5000 described later.

The alignment films 999a and 999b are disposed on both ends of the liquid crystal layer 216 and arrange the liquid crystal molecules in a certain direction. The alignment films 999a and 999b are made of, for example, a polymer material such as polyimide, and rubbing processing or the like is performed on the contact surface with the liquid crystal layer 216.

The liquid crystal layer 216 is disposed between the plurality of pixel electrodes 214 and the transparent conductive film 217 and modulates the laser light L according to an electric field formed by each pixel electrode 214 and the transparent conductive film 217. That is, when a voltage is applied to each pixel electrode 214 by the active matrix circuit of the driving circuit layer 914, an electric field is formed between the transparent conductive film 217 and each pixel electrode 214, and the arrangement direction of the liquid crystal molecules 216a changes according to the magnitude of the electric field formed in the liquid crystal layer 216. When the laser light L transmits through the transparent substrate 218 and the transparent conductive film 217 and is incident on the liquid crystal layer 216, the laser light L is modulated by the liquid crystal molecules 216a while passing through the liquid crystal layer 216, is reflected by the reflective film 215, is modulated again by the liquid crystal layer 216, and is emitted.

At this time, the voltage applied to each pixel electrode 214 is controlled by the spatial light modulator controller 502 (see FIG. 16) described later, and the refractive index of the portion sandwiched between the transparent conductive film 217 and each pixel electrode 214 in the liquid crystal layer 216 changes according to the voltage (the refractive index of the liquid crystal layer 216 at the position corresponding to each pixel changes). Due to the change in refractive index, the phase of the laser light L can be changed for each pixel of the liquid crystal layer 216 according to the applied voltage. That is, phase modulation corresponding to a hologram pattern can be applied by the liquid crystal layer 216 for each pixel. In other words, a modulation pattern serving as a hologram pattern imparting modulation can be displayed on the liquid crystal layer 216 of the reflective spatial light modulator 410. The wavefront of the laser light L that is incident on and transmits through the modulation pattern is adjusted, and the phase of the component in a predetermined direction orthogonal to the traveling direction in each light beam constituting the laser light L is shifted. Therefore, the laser light L can be modulated (for example, intensity, amplitude, phase, polarized light, or the like of the laser light L can be modulated) by appropriately setting the modulation pattern to be displayed on the reflective spatial light modulator 410.

[4f Lens Unit]

Figure 15:
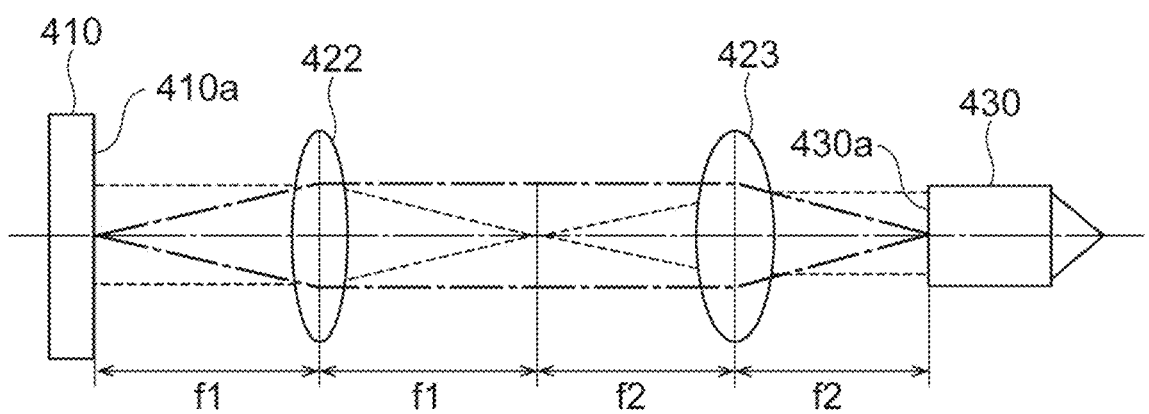
FIG. 15 is a diagram illustrating the optical arrangement of a reflective spatial light modulator, a 4f lens unit, and a condensing lens unit in the laser condensing unit of FIG. 11.

As described above, the pair of lenses 422 and 423 of the 4f lens unit 420 constitute a double-telecentric optical system in which the reflection surface 410a of the reflective spatial light modulator 410 and the entrance pupil plane 430a of the condensing lens unit 430 are in an imaging relationship. Specifically, as illustrated in FIG. 15, the distance of the optical path between the center of the lens 422 on the reflective spatial light modulator 410 side and the reflection surface 410a of the reflective spatial light modulator 410 is a first focal length f1 of the lens 422, the distance of the optical path between the center of the lens 423 on the condensing lens unit 430 side and the entrance pupil plane 430a of the condensing lens unit 430 is a second focal length f2 of the lens 423, and the distance of the optical path between the center of the lens 422 and the center of the lens 423 is the sum of the first focal length f1 and the second focal length f2 (i.e., f1+f2). The optical path between the pair of lenses 422 and 423 in the optical path from the reflective spatial light modulator 410 to the condensing lens unit 430 is a straight line.

In the laser processing device 200, from the viewpoint of increasing the effective diameter of the laser light L on the reflection surface 410a of the reflective spatial light modulator 410, the magnification M of the double-telecentric optical system satisfies 0.5<M<1 (reduction system). As the effective diameter of the laser light L on the reflection surface 410a of the reflective spatial light modulator 410 increases, the laser light L is modulated with a high-precision phase pattern. From the viewpoint of suppressing the optical path of the laser light L from the reflective spatial light modulator 410 to the condensing lens unit 430 from becoming long, 0.6 M 0.95 is more preferable. Here, (the magnification M of the double-telecentric optical system)= (the size of the image at the entrance pupil plane 430a of the condensing lens unit 430)/(the size of the object at the reflection surface 410a of the reflective spatial light modulator 410). In the case of the laser processing device 200, the magnification M of the double-telecentric optical system, the first focal length f1 of the lens 422, and the second focal length f2 of the lens 423 satisfy M=f2/f1.

From the viewpoint of reducing the effective diameter of the laser light L on the reflection surface 410a of the reflective spatial light modulator 410, the magnification M of the double-telecentric optical system may satisfy 1<M<2 (magnification system). As the effective diameter of the laser light L on the reflection surface 410a of the reflective spatial light modulator 410 decreases, the magnification of the beam expander 350 (see FIG. 9) is small. In the plane parallel to the XY plane, the angle α (see FIG. 11) between the optical axis of the laser light L incident on the reflective spatial light modulator 410 and the optical axis of the laser light L emitted from the reflective spatial light modulator 410 is reduced. From the viewpoint of suppressing the optical path of the laser light L from the reflective spatial light modulator 410 to the condensing lens unit 430 from becoming long, $1.05 \leq M \leq 1.7$ is more preferable.

Next, the main part of the laser processing device 200 according to an embodiment will be described in detail.

Figure 16:
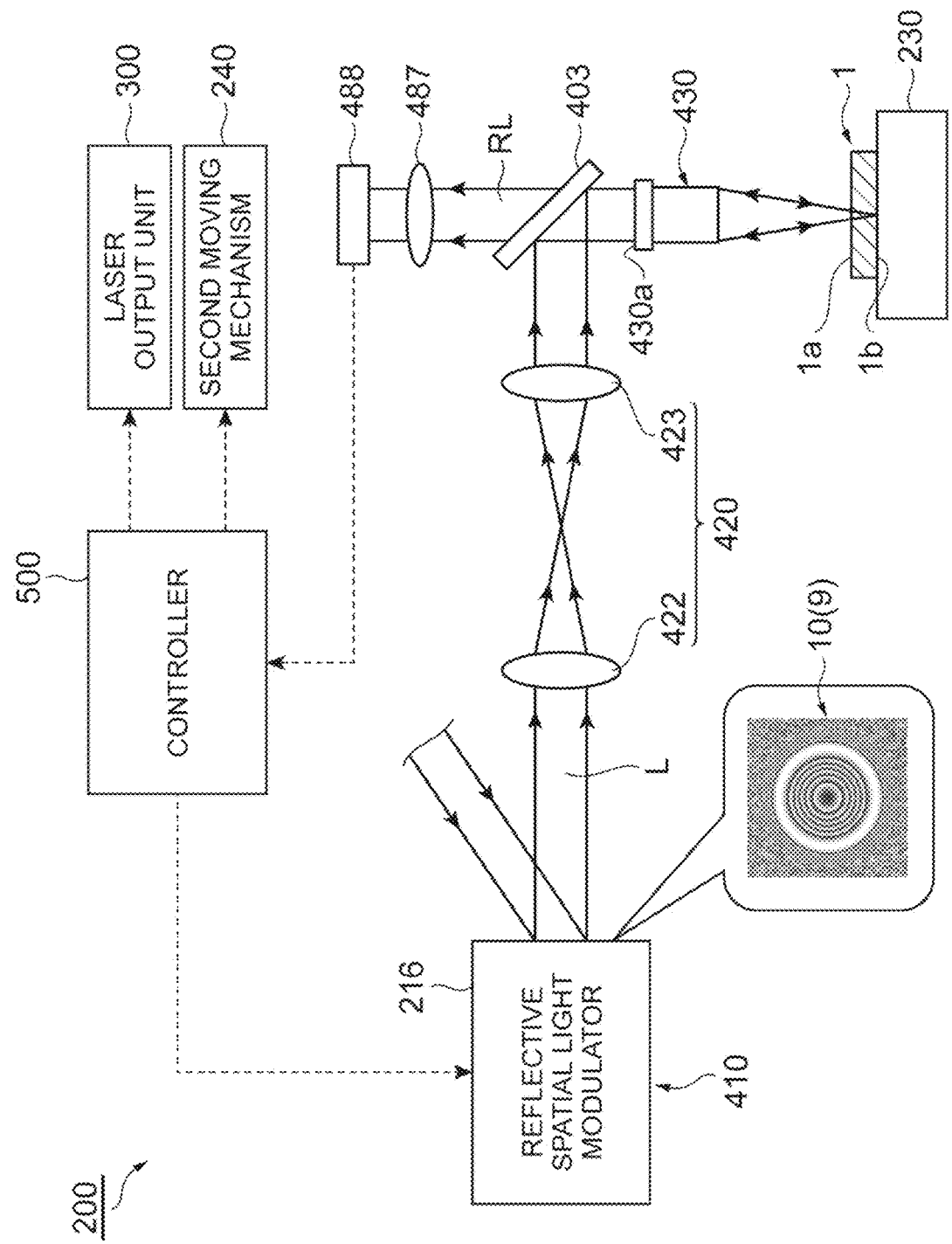
FIG. 16 is a schematic configuration diagram illustrating a main part of the laser processing device according to an embodiment.

FIG. 16 is a schematic configuration diagram illustrating the main part of the laser processing device 200 according to an embodiment. As illustrated in FIG. 16, the laser beam L incident on the liquid crystal layer 216 of the reflective spatial light modulator 410 and reflected is focused by the lens 422 which is a relay lens of the 4f lens unit 420, is collimated by the lens 423 which is a relay lens of the 4f lens unit 420, and is incident on the dichroic mirror 403. The laser light L reflected by the dichroic mirror 403 is incident on the condensing lens unit 430 and is irradiated onto the object 1 through the condensing lens unit 430.

The laser light L irradiated onto the object 1 is incident on the object 1 with the front face a as the laser beam entrance surface, advances toward the rear face 1b along the optical axis direction (Z-axis direction) within the object 1, and is reflected by the rear face 1b. Reflected light RL of the laser light L reflected by the rear face 1b travels toward the front face a along the optical axis direction within the object 1 and is emitted from the object 1 with the front face a as the laser light entrance surface. The reflected light RL emitted from the object 1 transmits through the dichroic mirror 403 and is then incident on the imaging surface of the observation camera 488 through the lens 487.

The pair of lenses 422 and 423 of the 4f lens unit 420 transfer (relay) the wavefront of the laser light L on the reflection surface 410a of the liquid crystal layer 216 onto the entrance pupil plane 430a of the condensing lens unit 430. Therefore, the reflection surface 410a of the liquid crystal layer 216 and the entrance pupil plane 430a of the condensing lens unit 430 form a conjugate relationship with each other. The 4f lens unit 420 constitutes an image-transfer optical system for transferring the image of the laser light L in the liquid crystal layer 216 onto the entrance pupil plane 430a.

The observation camera 488 constitutes a reflected light detector for detecting the reflected light RL reflected by the rear face 1b. The observation camera 488 captures a point image that is an image including a point image of the reflected light RL (also referred to as a beam spot, a rear face reflected image, or a condensing spot). The observation camera 488 outputs the captured point image to the controller 500.

The controller 500 controls a phase pattern 9 displayed on the liquid crystal layer 216 of the reflective spatial light modulator 410. The phase pattern 9 is the above-described modulation pattern and is a phase distribution that modulates the laser light L. The phase pattern 9 is set with reference to the reference position set on the liquid crystal layer 216. That is, the position serving as the reference at the time of displaying the phase pattern 9 in the liquid crystal layer 216 is set as the reference position (hereinafter simply referred to as "reference position"), and the position of the phase pattern 9 is set in a coordinate system determined based on the reference position. For example, the position of the phase pattern 9 is set as a coordinate value of two-dimensional coordinates with the reference position on the liquid crystal layer 216 as the origin. Here, the coordinate system of the liquid crystal layer 216 has the X direction and the Y direction as the coordinate axis direction, and one pixel of the liquid crystal layer 216 is set as one unit in each of the X direction and the Y direction.

When imaging the reflected light RL with the observation camera 488, the controller 500 executes a first process of causing the liquid crystal layer 216 to display a reflected light aberration correction pattern 10. The reflected light aberration correction pattern 10 is a phase pattern 9 for correcting aberration generated if the laser light L passes through the object 1 having twice the predetermined thickness. In other words, the reflected light aberration correction pattern 10 is the phase pattern 9 for correcting the aberration generated when passing through the object 1 having a medium thickness corresponding to twice the thickness. The reflected light aberration correction pattern 10 is a pattern including a plurality of concentric circles.

Doubling of the predetermined thickness includes not only completely double but also substantially 2 times or about 2 times. Twice the predetermined thickness includes manufacturing errors, design errors, and the like. For example, twice the predetermined thickness has a range of ±10% (when the predetermined thickness is α, (2α−0.1α) to (2α+0.1α)). Twice the predetermined thickness corresponds to the length of the path through which the laser light L is incident from the front face 1a, reflected by the rear face 1b, and is emitted from the front face 1a. For example, when the predetermined thickness of the object 1 is 775 μm, the phase pattern for correcting the aberration generated when irradiating from the front face a of the object 1 having a thickness of 1500 μm and condensing on the rear face 1b is the reflected light aberration correction pattern 10.

The controller 500 controls the operation of the second moving mechanism 240 and executes a second process of moving the condensing lens unit 430 in the direction of the optical axis to the position (detectable position) where the point image of the reflected light RL can be confirmed by the observation camera 488. For example, in the second process, the condensing lens unit 430 is moved such that the focal point of the condensing lens unit 430 is positioned at the rear face 1b or in the vicinity of the rear face 1b. The vicinity of the rear face 1b is substantially the rear face 1b position, the vicinity of the rear face 1b position, or the periphery of the rear face 1b position. The position at which the point image of the reflected light RL can be confirmed is a position at which the point image is focused to a certain extent or more and recognition or image processing thereof (described later) concerning whether the point image is a rotationally symmetric optical image is possible.

After the second process, in a state in which the reflected light aberration correction pattern 10 is displayed on the liquid crystal layer 216 by the first process, the controller 500 executes a third process including a process of controlling the operation of the laser output unit 300 to generate the laser light L from the laser oscillator 310 (see FIG. 9) to irradiate the object 1 and a process of acquiring, from the observation camera 488, the point image of the reflected light RL captured by the observation camera 488 in response to the irradiation.

FIG. 17 is a schematic sectional view for explaining each condensing state at the time of rear face reflection where the laser light L is reflected by the rear face 1b. Each light condensing state in FIG. 17 is an example of a case in which the focal point of the condensing lens unit 430 is positioned on the rear face 1b. FIG. 18 is a photograph showing a point image captured by the observation camera 488 in each condensing state of FIG. 17.

FIGS. 17(a) and 18(a) illustrate the condensing state of the laser light L when the aberration correction is not performed by the reflective spatial light modulator 410. FIGS. 17(b) and 18(b) illustrate the condensing state of the laser light L in a case in which the reflective spatial light modulator 410 performs aberration correction (medium thickness correction) for correcting aberration occurring in the event of the laser light L being transmitted through the object 1 having a predetermined thickness. FIGS. 17(c) and 18(c) illustrate the condensing state of the laser light L in a case in which the reflective spatial light modulator 410 performs aberration correction (medium thickness twice correction) for correcting aberration occurring in the event of the laser light L being transmitted through the object 1 having twice the predetermined thickness.

As illustrated in FIG. 17(a), when the aberration correction is not performed, the outer peripheral portion of the laser light L is shifted to a position deeper than the inner peripheral portion and is condensed. As illustrated in FIG.

17(b), when the medium thickness is corrected, all the components of the laser light L are condensed at one point on the rear face 1b. Therefore, when the reflected light RL, which further transmits through the medium of the predetermined thickness after being reflected by the rear face 1b and is emitted from the front face 1a, is condensed by the lens 487, it is blurred by the influence of aberration and does not condense on one point. As a result, as illustrated in FIGS. 18(a) and 18(b), point images such as sufficient brightness and size cannot be confirmed in the image of the reflected light RL captured by the observation camera 488.

On the other hand, as illustrated in FIG. 17(c), when the medium thickness twice correction is performed, the outer peripheral portion of the laser light L is shifted to a shallower position than the inner peripheral portion and is condensed. When the media thickness twice correction is performed, the reflected light RL, which further transmits through the medium of the predetermined thickness after being reflected by the rear face 1b and is emitted from the front face a, is cleanly condensed at one point when condensed by the lens 487. As a result, as illustrated in FIG. 18(c), in the image of the reflected light RL captured by the observation camera 488, it is possible to confirm a point image such as brightness and size sufficient enough for the controller 500 to make determination and adjustment described later.

The controller 500 repeats the third process one or more times while changing the position of the reflected light aberration correction pattern 10 on the liquid crystal layer 216 and performs a fourth process of acquiring a plurality of point images by the observation camera 488.

Here, the controller 500 determines whether there is a shift (hereinafter referred to as "image-transfer position shift") between the center position of the entrance pupil plane 430a and the center position of the image of the laser light L having been transferred onto the entrance pupil plane 430a by the 4f lens unit 420, based on the point image captured by the observation camera 488. In addition, the controller 500 adjusts the reference position of the phase pattern 9 so as to reduce or eliminate the image-transfer position shift. Hereinafter, the principle or phenomenon relating to the determination of the image-transfer shift position and the adjustment of the reference position will be described.

Figure 19:
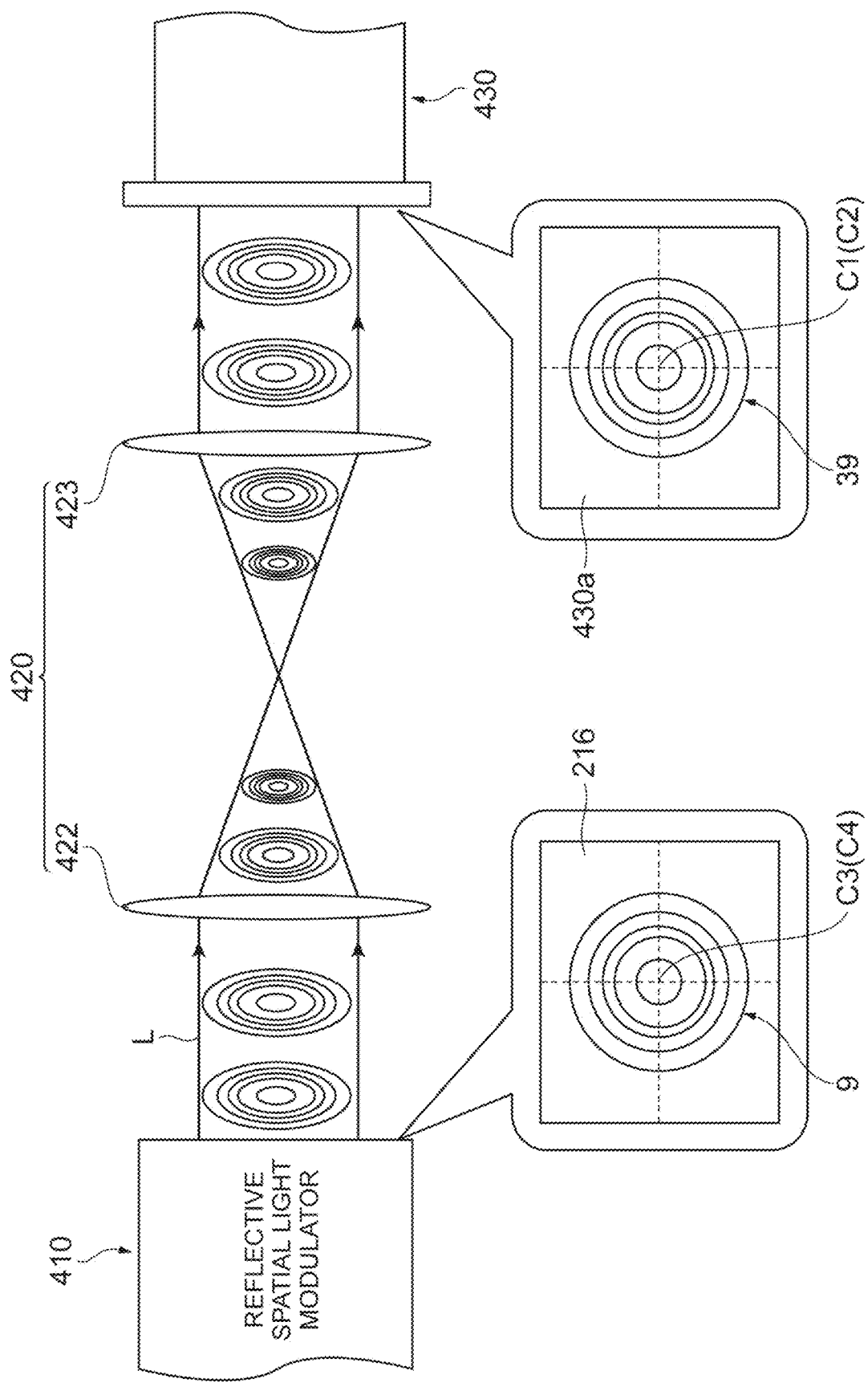
FIG. 19 is a schematic diagram for explaining a state in which no image-transfer position shift occurs.
Figure 20:
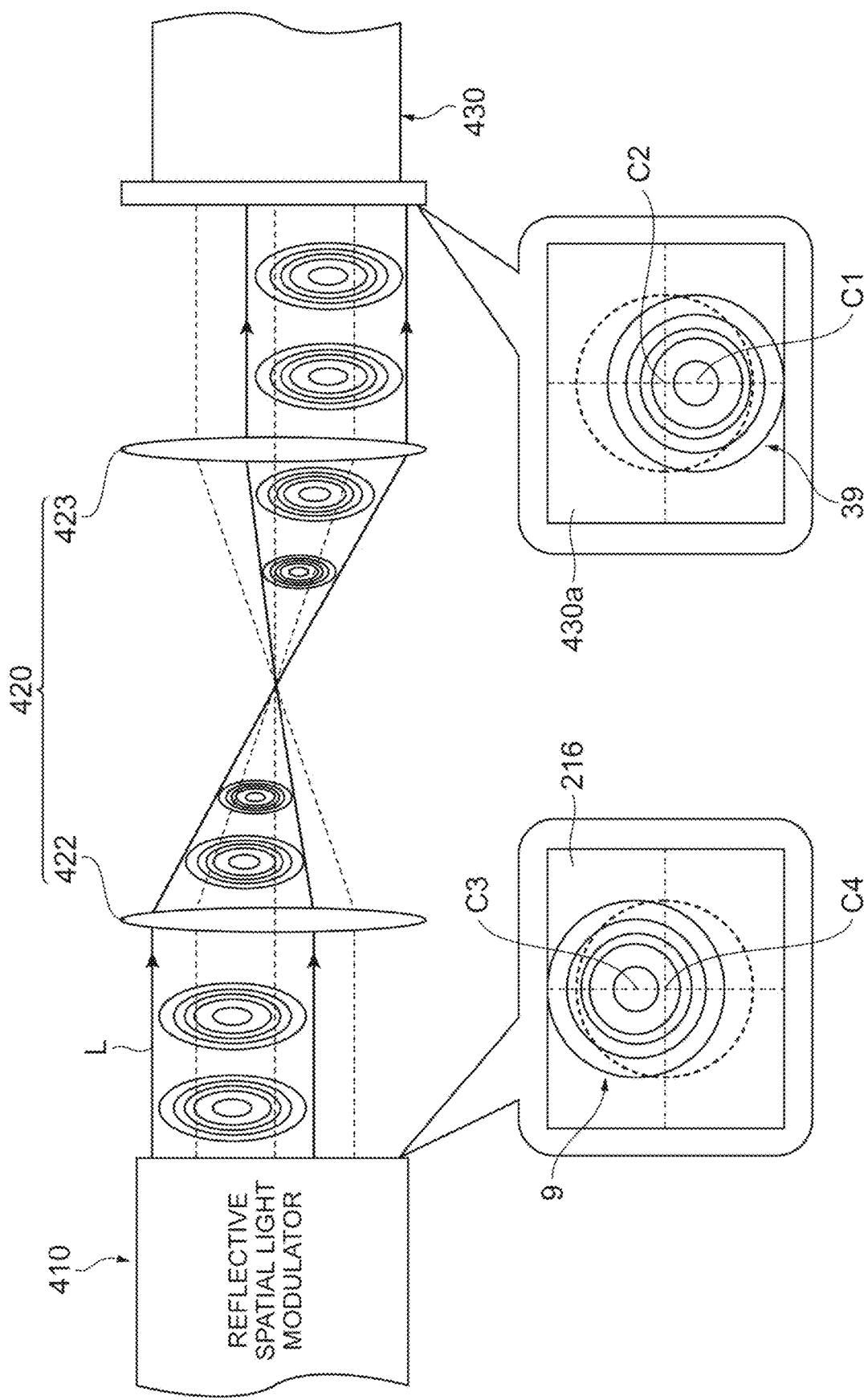
FIG. 20 is a schematic diagram for explaining a state in which an image-transfer position shift occurs.

FIG. 19 is a schematic diagram for explaining a state in which no image-transfer position shift occurs. FIG. 20 is a schematic diagram for explaining a state in which an image-transfer position shift occurs. As illustrated in FIG. 19, when no image-transfer position shift occurs, the 4f lens unit 420 transfers the image of the laser light L reflected by the liquid crystal layer 216 of the reflective spatial light modulator 410 to the condensing lens unit 430 as it is. The center position C1 of the image 39 of the laser light L having been transferred onto the entrance pupil plane 430a coincides with the center position C2 of the entrance pupil plane 430a. The center position C3 of the phase pattern 9 coincides with the optical axis center C4 of the liquid crystal layer 216, that is, the reference position of the phase pattern 9 in the liquid crystal layer 216 is set to the optical axis center C4.

On the other hand, as illustrated in FIG. 20, when the image-transfer position shift occurs, the center position C3 as the reference position of the phase pattern 9 is shifted from the optical axis center C4 of the liquid crystal layer 216. In other words, when the center position C3 of the phase pattern 9 is set to be shifted from the optical axis center C4, the center position C1 of the image 39 of the laser light L that is transferred onto the entrance pupil plane 430a is shifted (mismatched) with respect to the center position C2 of the entrance pupil plane 430a. In this case, it is found that the beam intensity center is shifted and coma aberration occurs. For example, when the center position C3 of the phase pattern 9 in the liquid crystal layer 216 is shifted by one pixel from the optical axis center C4, there is a possibility that the image-transfer position shift of 20 μm occurs, which may affect the processing quality.

Figure 21:
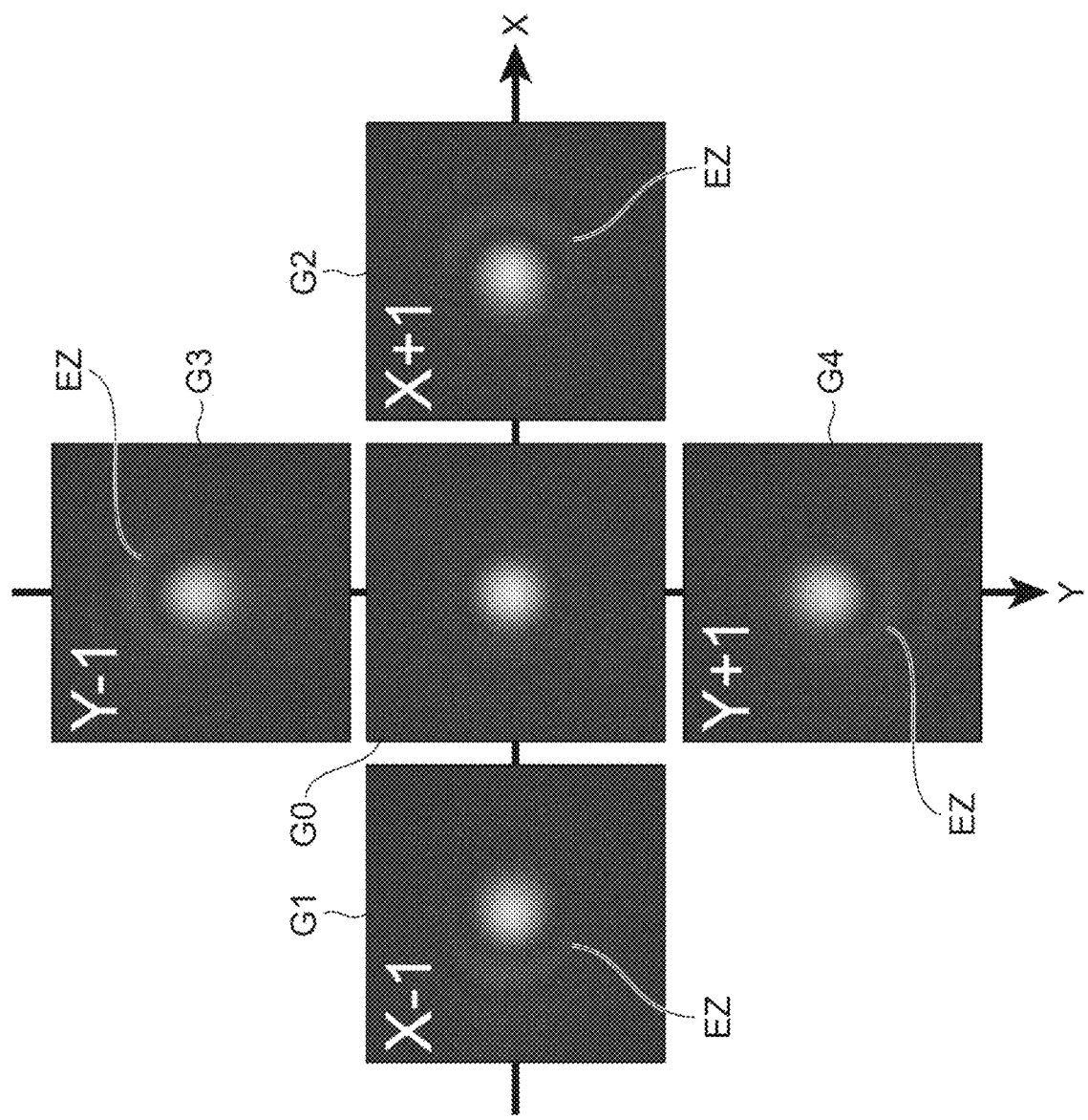
FIG. 21 is a diagram illustrating an example of a point image when a position of a phase pattern displayed on a liquid crystal layer is changed.

FIG. 21 is a diagram illustrating an example of the point image when the position of the phase pattern 9 displayed on the liquid crystal layer 216 is changed. A point image G0 is a point image in a case in which the reference position of the phase pattern 9 is set at the optical axis center C4. A point image G1 is a point image in a case in which the reference position is shifted by one pixel toward the minus side in the X direction of the coordinate system of the liquid crystal layer 216 with respect to the optical axis center C4. A point image G2 is a point image in a case in which the reference position is shifted by one pixel toward the plus side in the X direction of the coordinate system of the liquid crystal layer 216 with respect to the optical axis center C4. A point image G3 is a point image in a case in which the reference position is shifted by one pixel toward the minus side in the Y direction of the coordinate system of the liquid crystal layer 216 with respect to the optical axis center C4. A point image G4 is a point image in a case in which the reference position is shifted by one pixel toward the plus side in the Y direction of the coordinate system of the liquid crystal layer 216 with respect to the optical axis center C4. In the point image G0, there is no image-transfer position shift, and in the point images G1 to G4, the image-transfer position shift occurs.

As illustrated in FIG. 21, since it is found that the coma aberration occurs in the point images G1 to G4 in which the image-transfer position shift occurs as described above, the point image is not a rotationally symmetric optical image due to the coma aberration. For example, in the point images G1 to G4, the point image is eccentric, an arcuate image EZ is included on the outer periphery side, and a part of the point image in the peripheral direction has a shape that is more blurred than the other part. On the other hand, in the point image G0 where no image-transfer position shift occurs, the influence of coma aberration is not observed, and the point image is a rotationally symmetric optical image.

The rotational symmetry means symmetry that overlaps itself when rotating around a certain center by 360/n° (n is an integer of 2 or more). The rotationally symmetric point images include those substantially rotationally symmetric as well as those perfectly rotationally symmetric. The rotationally symmetric point images include a point image not eccentric, a point image not including an arcuate image EZ on the outer peripheral side, a point image in which a part in the peripheral direction is not more blurred than the other part, and a point image including at least one of these.

Figure 22:
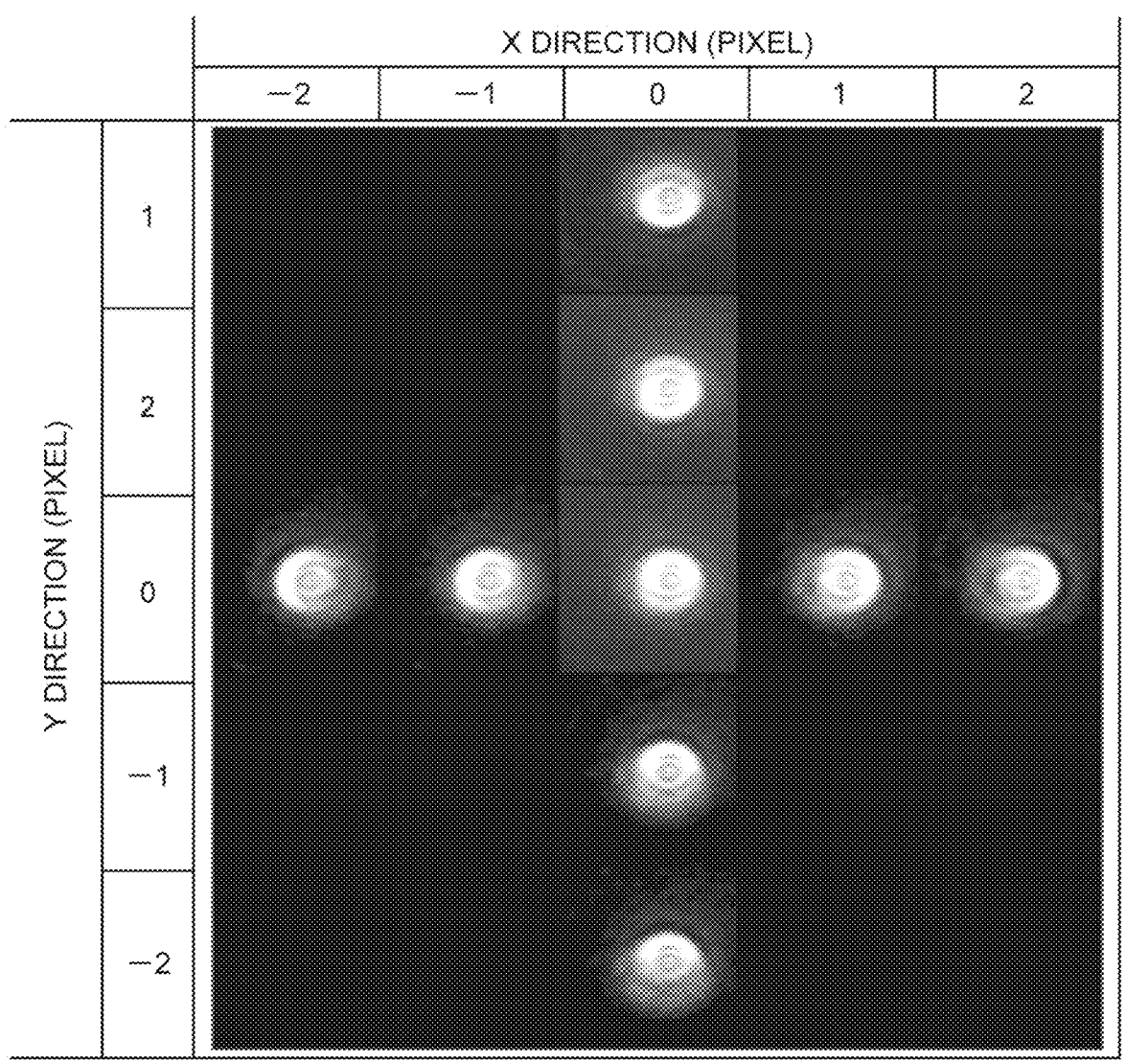
FIG. 22 is another diagram illustrating an example of a point image when a position of a phase pattern displayed on a liquid crystal layer is changed.

FIG. 22 is another diagram illustrating an example of the point image when the position of the phase pattern 9 displayed on the liquid crystal layer 216 is changed. Regarding the numbers in the X direction in FIG. 22, "0" indicates a case in which the reference position coincides with the optical axis center C4 in the X direction, and "−2", "−1", "1", and "2" indicate cases where the reference position in the X direction is offset by "−2 pixels", "4 pixel", "1 pixel", and "2 pixels" with respect to the optical axis center C4, respectively. Similarly, regarding the numbers in the Y direction in FIG. 22, "0" indicates a case in which the reference position coincides with the optical axis center C4 in the Y direction, and "−2", "−1", "1", and "2" indicate cases where the reference position in the Y direction is offset by "−2 pixels", "−1 pixel", "1 pixel", and "2 pixels" with respect to the optical axis center C4, respectively. FIG. 22 illustrates a point image at a normal time when the reference position coincides with the optical axis center C4, each point image in a case in which the reference position is offset only in the X direction from the normal time, and each point image in a case in which the reference position is offset only in the Y direction from the normal time.

As illustrated in FIG. 22, when the reference position coincides with the optical axis center C4 (that is, no image-transfer position shift occurs), the point image becomes a rotationally symmetric optical image. When the reference position is shifted from the optical axis center C4 (that is, the image-transfer position shift occurs), the point image collapses to become a rotationally asymmetric optical image. Further, as the shift amount of the reference position from the optical axis center C4 increases (that is, as the shift amount of the image-transfer position shift increases), the shift of the point image from the rotational symmetry in the optical image is large.

From the knowledge of the above principle or phenomenon, as illustrated in FIG. 16, the controller 500 determines whether there is the image-transfer position shift based on the point image captured by the observation camera 488. Specifically, when the point image of the reflected light RL in the point image is not a rotationally symmetric optical image, the controller 500 determines that there is the image-transfer position shift. Whether it is the rotationally symmetric optical image may be recognized, for example, from the point image by the geometric method, and may be recognized by known image recognition processing such as pattern recognition. For example, at least one of the point images illustrated in FIG. 21 or 22 is stored in advance, and whether it is the rotationally symmetric optical image is recognized by using the pattern matching method using the stored point image.

In addition, the controller 500 adjusts the reference position in the liquid crystal layer 216 based on the point image captured by the observation camera 488. The controller 500 offset (shifts) the reference position in the liquid crystal layer 216 such that the point image of the reflected light RL in the point image becomes the rotationally symmetric optical image. Specifically, the controller 500 calculates the optical axis center C4 in the liquid crystal layer 216 from the plurality of point images acquired in the fourth process. For example, the controller 500 obtains the point image when it is the rotationally symmetric optical image from the plurality of point images, and obtains the position of the reflected light aberration correction pattern 10 on the liquid crystal layer 216 at the point image. Based on the position of the reflected light aberration correction pattern JO at this time, the optical axis center C4 is calculated. Then, the controller 500 offsets the reference position to the calculated optical axis center C4.

A monitor is connected to the controller 500. The monitor can display the point image of the reflected light RL captured by the observation camera 488. The monitor can display the phase pattern 9 to be displayed on the liquid crystal layer 216 by the spatial light modulator controller 502. The monitor can display, as a log, a determination result as to whether there is the image-transfer position shift by the controller 500. The monitor can display, as a log, the adjustment result of the reference position by the controller 500.

Figure 23:
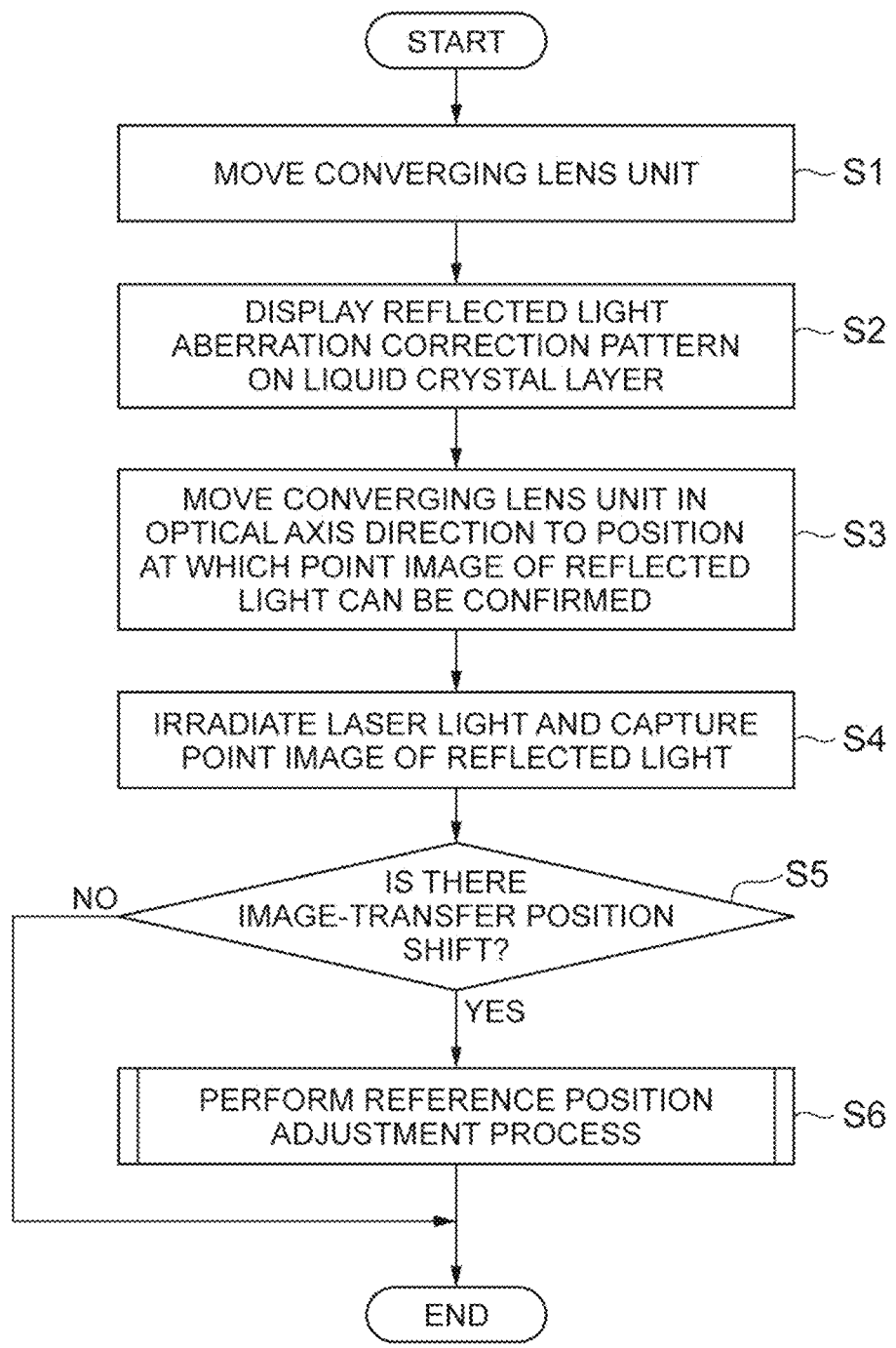
FIG. 23 is a flowchart showing a laser light irradiation method according to an embodiment.
Figure 24:
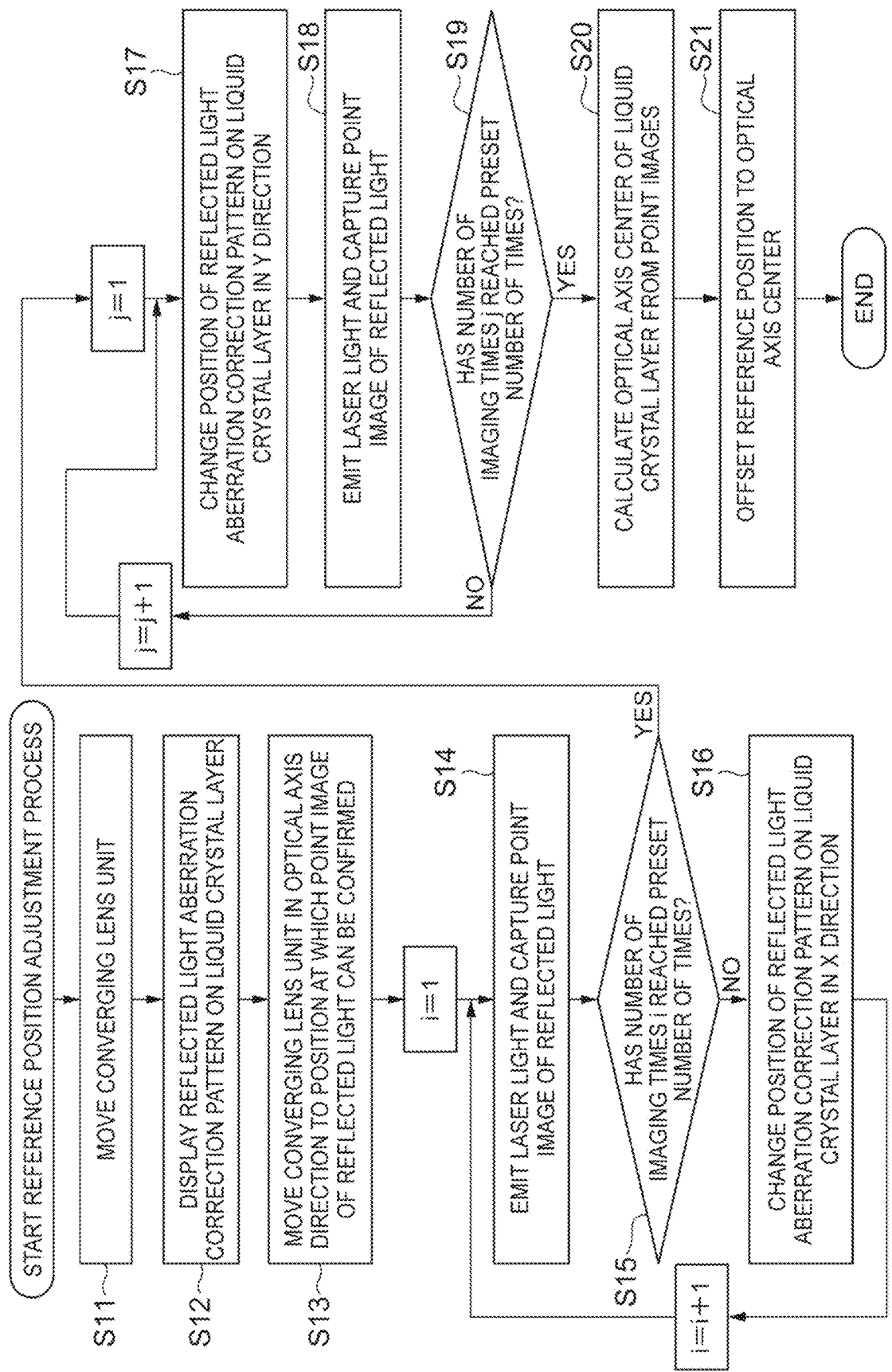
FIG. 24 is a flowchart showing a reference position adjustment process of FIG. 23.

Next, an example of the laser light irradiation method according to this embodiment will be described with reference to the flowcharts of FIGS. 23 and 24.

The laser beam irradiation method according to this embodiment can be used as an inspection direction or adjustment method of the laser processing device 200 and is implemented as, for example, a check mode at a periodic inspection. In the laser light irradiation method according to this embodiment, the controller 500 executes the following processing. That is, first, the laser condensing unit 400 is moved along the Z-axis direction by the second moving mechanism 240, and the condensing lens unit 430 is moved with respect to the object 1 such that the focal position of the observation camera 488 becomes the front face 1a (reticle reference position) (step S1).

The reflected light aberration correction pattern 10 is displayed on the liquid crystal layer 216 (step S2). The laser condensing unit 400 is moved along the Z-axis direction by the second moving mechanism 240, and the condensing lens unit 430 is moved in the optical axis direction with respect to the object 1 to the position at which the point image of the reflected light RL can be confirmed, which is the position defocused from the reticle reference position (step S3).

In a state in which the reflected light aberration correction pattern 10 is displayed on the liquid crystal layer 216, the laser light L is emitted from the laser oscillator 310, and the laser light L is irradiated onto the object 1. The point image of the reflected light RL is captured by the observation camera 488 according to the irradiation (step S4). In step S4, the laser output unit 300 (the λ/2 wave plate unit 330 and the polarizing plate unit 340) are controlled so that the modified region 7 is not formed on the object 1 by the irradiation of the laser light L, and the output of the laser light L is adjusted to an output that is smaller than a processing threshold value of the object 1.

Based on the captured point image, it is determined whether there is the image-transfer position shift (step S5). When the point image included in the point image is the optical image of the rotation center, it is NO in step S5, it is determined that there is no image-transfer position shift, and the process is ended as it is. On the other hand, when the point image is not the optical image of the rotation center, it is YES in step S5. Since there is the image-transfer position shift, the reference position adjustment process for adjusting the reference position of the phase pattern 9 is executed (step S6).

In the reference position adjustment process, first, as in step S1, the condensing lens unit 430 is moved relative to the object 1 such that the focal position of the observation camera 488 becomes the reticle reference (step S11). As in step S2, the reflected light aberration correction pattern 10 is displayed on the liquid crystal layer 216 (step S12). As in step S3, the condensing lens unit 430 is moved in the optical axis direction with respect to the object 1 to the position at which the point image of the reflected light RL reflected by the rear face 1b of the object 1 can be confirmed (step S13).

As in step S4, in a state in which the reflected light aberration correction pattern 10 is displayed on the liquid crystal layer 216, the laser light L is emitted from the laser oscillator 310, and the laser light L is irradiated onto the object 1. The point image of the reflected light RL is captured by the observation camera 488 according to the irradiation (step S14).

It is determined whether the number of imaging times i, which is the number of times of processing in step S14, has reached a preset predetermined number of times (=integer of 2 or more) (step S15). If NO in step S15, the position of the reflected light aberration correction pattern 10 on the liquid crystal layer 216 is changed by one pixel along the X direction, and the process returns to step S14 (step S16).

If YES in step S15, the position of the reflected light aberration correction pattern 10 on the liquid crystal layer 216 is changed by one pixel along the Y direction (step S17). As in step S4, in a state in which the reflected light aberration correction pattern 10 is displayed on the liquid crystal layer 216, the laser light L is emitted from the laser oscillator 310, and the laser light L is irradiated onto the object 1. The point image of the reflected light RL is captured by the observation camera 488 according to the irradiation (step S18). It is determined whether the number of imaging times j, which is the number of times of processing in step S18, has reached a preset predetermined number of times (=integer of 2 or more) (step S19). If NO in step S19, the process returns to step S17.

If YES in step S19, the optical axis center C4 in the liquid crystal layer 216 is calculated from the plurality of point images acquired in step S14 and step S18 (step S20). For example, in step S20, the point image when it is the rotationally symmetric optical image among the plurality of point images is obtained, and the center position of the reflected light aberration correction pattern 10 on the liquid crystal layer 216 at the point image is calculated as the optical axis center C4. Then, the reference position is offset to the calculated optical axis center C4 (step S21). Therefore, the position of the image 39 of the laser light L that has been transferred onto the entrance pupil plane 430a is corrected to the state in which the image-transfer position shift is reduced and eventually does not occur.

In the above, the controller 500 constitutes a position determining unit and a position adjustment unit. Step S12 constitutes a first step. Steps S14 and S18 constitute a second step. Steps S20 and S21 constitute a third step.

As described above, in the laser processing device 200 according to this embodiment, the reflected light RL of the laser light L incident from the front face a of the object 1 and reflected by the rear face 1b is detected by the observation camera 488. At this time, the aberration occurring in the reflected light RL due to transmission through the object 1 (transmission from the front face a to the rear face 1b and transmission from the rear face 1b to the front face a) can be corrected through modulation with the reflected light aberration correction pattern 10 of the reflective spatial light modulator 410. Here, when there is the image-transfer position shift, for example, since the laser light L is not appropriately condensed by the condensing lens unit 430, it is found that the influence of aberration such as coma aberration appears in the reflected light RL captured by the observation camera 488. On the other hand, it is found that when there is no image-transfer position shift, the reflected light RL captured by the observation camera 488 has little or no influence of aberration such as coma aberration or the like. Therefore, based on the point image captured by the observation camera 488, it is possible to grasp the image-transfer position shift.

In the laser processing device 200, the controller 500 determines whether there is an image-transfer position shift based on the point image of the observation camera 488. Therefore, the controller 500 can automatically determine the presence or absence of the image-transfer position shift.

As described above, it is found that when there is no image-transfer position shift, the point image of the reflected light RL captured by the observation camera 488 becomes the optical image to be rotated, and when there is the image-transfer position shift, it is difficult to form the rotationally symmetric optical image by the influence of coma aberration or the like. Therefore, in the laser processing device 200, when the point image of the reflected light RL in the point image captured by the observation camera 488 is not the rotationally symmetric optical image, the controller 500 determines that there is the image-transfer position shift. Therefore, it is possible to accurately determine the presence or absence of the image-transfer position shift.

In the laser processing device 200, the controller 500 offsets the reference position in the liquid crystal layer 216 based on the point image by the observation camera 488. This makes it possible to automatically adjust the center position C1 of the image 39 of the laser light L that has been transferred onto the entrance pupil plane 430a, for example, so as to reduce the image-transfer position shift. As a result, the deterioration of the processing quality can be suppressed.

As described above, it is found that when there is no image-transfer position shift, the point image of the reflected light RL captured by the observation camera 488 becomes the optical image to be rotated. Therefore, in the laser processing device 200, the controller 500 offsets the reference position of the liquid crystal layer 216 such that the point image of the reflected light RL in the point image captured by the observation camera 488 becomes the rotationally symmetric optical image. This makes it possible to adjust the center position C1 of the image 39 of the laser light L that has been transferred onto the entrance pupil plane 430a so as to coincide with the center position C2 of the entrance pupil plane 430a, thereby reducing the image-transfer position shift.

In the laser processing device 200, the controller 500 executes the first to fourth processes. In the first process, the reflected light aberration correction pattern 10 is displayed on the liquid crystal layer 216. In the second process, the condensing lens unit 430 is moved along the optical axis to the position at which the observation camera 488 can confirm the image transfer of the reflected light RL. In the third process, after the second process, in a state in which the reflected light aberration correction pattern 10 is displayed on the liquid crystal layer 216 by the first process, the object 1 is irradiated with the laser light L and the point image of the reflected light RL is acquired from the observation camera 488 according to the irradiation. In the fourth process, the third process is repeated one or a plurality of times while changing the position of the reflected light aberration correction pattern 10 on the liquid crystal layer 216, and a plurality of point images are acquired. Then, the controller 500 calculates the optical axis center C4 in the liquid crystal layer 216 based on the acquired plurality of point images and offsets the reference position to the optical axis center C4. In this case, it is possible to specifically realize adjustment for reducing the image-transfer position shift.

According to the laser light irradiation method using the laser processing device 200, it is possible to grasp the image-transfer position shift by the detection result of the reflected light RL (the point image of the observation camera 488). Further, by offsetting the reference position from the detection result of the reflected light RL, it is possible to adjust the position of the image 39 of the laser light L that has been transferred onto the entrance pupil plane 430a so as to reduce or eliminate the image-transfer position shift.

In this embodiment, since the reflected light RL reflected by the rear face 1b is used, the laser light L transmitted through the inside of the object 1 is detected, thereby reducing the influence of unnecessary ghost light. It is possible to accurately determine the image-transfer position shift and to adjust the reference position.

In general, a method of actually performing laser processing on the object 1, determining the image-transfer position shift from the processing quality (for example, crack extension amount) of the object 1 after the laser processing, and adjusting the reference position of the liquid crystal layer 216 is employed. In this regard, in this embodiment, simple operation can be performed, for example, during periodic condition check. In addition, before performing the reference position adjustment process, the presence or absence of the image-transfer position shift is first determined. Therefore, it is possible to prevent the reference position adjustment process from being performed even when there is no image-transfer position shift and to perform the efficient operation.

FIGS. 25 and 26 are tables showing a relationship between the reference position of the liquid crystal layer 216 and the laser processing result. Here, the laser light L is scanned along the line 5 with the front face a as the laser light entrance surface while the aberration correction of the laser light L is performed by the reflective spatial light modulator 410, and the processing quality of the cutting laser processing for condensing the laser light L inside the object 1 is evaluated as the laser processing result. "EXCELLENT" in the drawing indicates a case in which the crack reaching the rear face 1b occurred and the object 1 can be cut with accuracy. "GOOD" in the drawing indicates a case in which the crack reaching the rear face 1b occurred but gouging (traces like tears) occurred on a part of the cut face. "WRONG" in the drawing indicates a case in which the crack reaching the rear face 1b do not occur.

The depth in the drawing is the distance of the condensing point P from the front face 1a. The forward path is a case in which one direction along the line 5 is set as the scanning direction, and the returning path is a case in which the other direction along the line 5 is set as the scanning direction. The numerals in the Y direction in FIG. 25 and the numbers in the X direction in FIG. 26 are the same as those described above with reference to FIG. 22. The X direction corresponds to the processing progress direction (scanning direction).

As illustrated in FIGS. 25 and 26, as the reference position approaches the optical axis center C4, cracks reaching the rear face 1b are likely to occur even if the condensing point P is formed at a shallow position (on the front face a side) of the object 1, and it can be confirmed that machining quality is improved. In addition, with respect to the shift of the reference position from the optical axis center C4 in the Y direction, it can be confirmed that the shift of the reference position from the optical axis center C4 in the X direction, which is the processing progress direction, severely influences the processing quality.

Although the preferable embodiments have been described above, the present invention is not limited to the above embodiments and may be modified within the range not changing the gist described in each claim or may be applied to other ones.

The above-described embodiment is not limited to the embodiment of forming the modified region 7 within the object 1, but may also perform other laser processing such as ablation. The above-described embodiment is not limited to the laser processing device used for laser processing for condensing the laser light L within the object 1, and may be a laser processing device used for laser processing for condensing the laser light L on the front faces 1a and 3 or the rear face 1b of the object 1. The device to which the present invention is applied is not limited to the laser processing device, and can be applied to various laser light irradiation devices as long as they irradiate the object with the laser light L. In the above-described embodiment, although the line 5 is set as the line to be irradiated, the line to be irradiated is not limited to the line 5, and any line may be used as long as the laser light L to be irradiated is aligned.

In the above-described embodiment, the imaging optical system constituting the double-telecentric optical system in which the reflection surface 410a of the reflective spatial light modulator 410 and the entrance pupil plane 430a of the condensing lens unit 430 are in an imaging relationship is not limited to the pair of lenses 422 and 423, and may include a first lens system (for example, a cemented lens, three or more lenses, or the like) on the reflective spatial light modulator 410 side and a second lens system (for example, a cemented lens, three or more lenses, or the like) on the condensing lens unit 430 side, or the like.

In the above-described embodiment, the relay magnifications of the lens 422, the lens 423, and the lens 463 may be an arbitrary magnification. Although the above-described embodiment includes the reflective spatial light modulator 410, the spatial light modulator is not limited to the reflective type, and may be provided with a transmissive spatial light modulator. In the above-described embodiment, the front face a which is the main face is set as the laser light entrance surface and the rear face 1b which is the main face of the opposite side is the opposite surface, but the rear face 1b may be the laser light entrance surface and the front face a may be the opposite surface.

In the above-described embodiment, the condensing lens unit 430 and the pair of distance measurement sensors 450 are attached to the end portion 401d of the housing 401 in the Y-axis direction, but may be attached so as to be biased toward the end portion 401d side from the center position of the housing 401 in the Y-axis direction. The reflective spatial light modulator 410 is attached to the end portion 401c of the housing 401 in the Y-axis direction, but may be attached so as to be biased toward the end portion 401c side from the center position of the housing 401 in the Y-axis direction. In addition, the distance measurement sensor 450 may be disposed only on one side of the condensing lens unit 430 in the X-axis direction.

Figure 27:
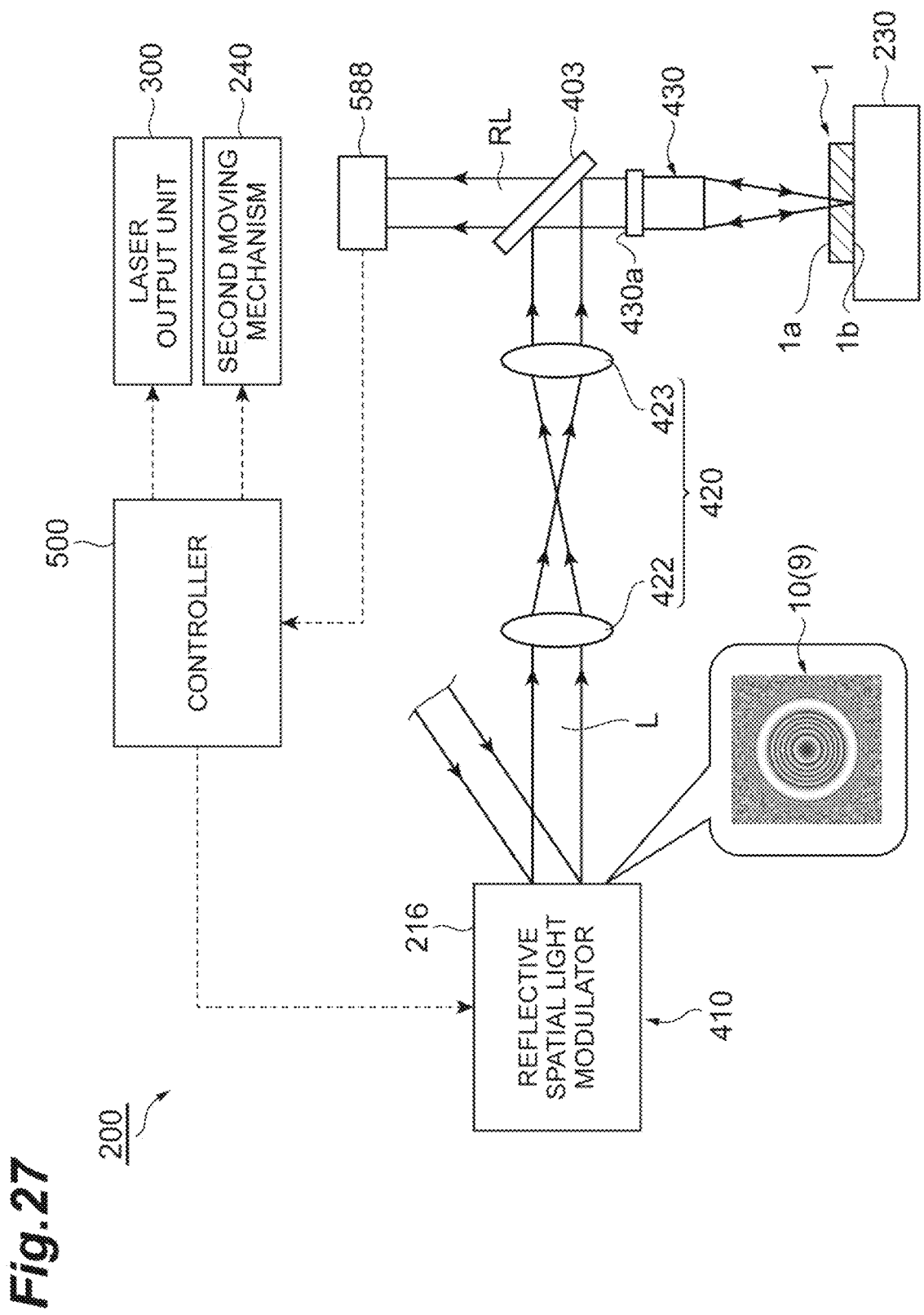
FIG. 27 is a schematic configuration diagram illustrating a main part of the laser processing device according to a modified example.

In the above-described embodiment, the observation camera 488 is used as the reflected light detector, but the reflected light detector is not particularly limited as long as the reflected light detector can detect the reflected light RL. In the above-described embodiment, instead of the observation camera 488 and the lens 487, as illustrated in, for example, FIG. 27, the wavefront sensor 588 for detecting the wavefront of the reflected light RL may be provided as the reflected light detector. The wavefront sensor includes, for example, a microlens array and an imaging element, and acquires a local phase gradient from a condensing spot image position by each microlens. As the wavefront sensor, a Shack-Hartmann wavefront sensor (manufactured by THORLABS, WFS 150-5C) can be used.

In this modified example, when the wavefront of the reflected light RL detected by the wavefront sensor is not a plane, the controller 500 may determine that there is an image-transfer position shift. Therefore, it is possible to accurately determine the presence or absence of the image-transfer position shift. In addition, the controller 500 may offset the reference position such that the wavefront of the reflected light RL detected by the wavefront sensor becomes a plane. This makes it possible to adjust the center position C1 of the image 39 of the laser light L that has been transferred onto the entrance pupil plane 430a so as to coincide with the center position C2 of the entrance pupil plane 430a, thereby reducing or eliminating the image-transfer position shift. This is because it is found that the reflected light RL becomes a plane wave (a plane in which the equiphase surface of the wave is a plane) when there is no image-transfer position shift, and the reflected light RL does not become a plane wave when there is the image-transfer position shift. The plane is not limited to a complete plane, but may be substantially planar. The plane includes a substantially flat surface and an approximately flat surface.

Alternatively, in the above-described embodiment, for example, the detector for detecting the coma aberration component may be provided as the reflected light detector. In this modified example, when the detected coma aberration component is not 0 or a predetermined value or less, the controller 500 may determine that there is the image-transfer position shift. In addition, the controller 500 may offset the reference position such that the detected coma aberration component becomes 0 or a predetermined value or less.

In the above-described embodiment, both the determination of the image-transfer position shift and the adjustment (offset) of the reference position are performed by the controller 500, but only the determination of the image-transfer position shift may be performed, or only the adjustment of the reference position may be performed. Further, instead of or in addition to the determination of the image-transfer position shift by the controller 500, the point image (the detection result of the reflected light RL) may be displayed on the monitor, and the operator may visually determine the image-transfer position shift based on the point image. Instead of or in addition to the adjustment of the reference position by the controller 500, the point image may be displayed on the monitor, and the operator may visually adjust the reference position based on the point image. The controller 500 may be one electronic control unit or may be a plurality of electronic control units.

REFERENCE SIGNS LIST 1 object to be processed (object)
1a, 3 front face (laser light entrance surface)
1b rear face (opposite surface)
9 phase pattern
10 reflected light aberration correction pattern
100, 200 laser processing device (laser light irradiation device)
216 liquid crystal layer (display unit)
240 second moving mechanism (moving mechanism)
310 laser oscillator (laser light source)
410 reflective spatial light modulator (spatial light modulator)
420 4f lens unit (image-transfer optical system)
430 condensing lens unit (objective lens)
430a entrance pupil plane
488 observation camera (reflected light detector, camera)
500 controller (position determining unit, position adjustment unit)
588 wavefront sensor
L laser light
RL reflected light

The invention claimed is:

1. A laser light irradiation device for irradiating an object having a predetermined thickness with laser light, the laser light irradiation device comprising:
a laser light source configured to generate the laser light;
a spatial light modulator comprising a display configured to display a phase pattern, the spatial light modulator configured to cause the laser light generated by the laser light source to enter the display, modulate the laser light according to the phase pattern, and emit the laser light from the display;
an objective lens configured to condense the laser light emitted from the spatial light modulator at the object;
an image-transfer optical system configured to transfer an image of the laser light on the display of the spatial light modulator to an entrance pupil plane of the objective lens;
a reflected light detector configured to detect reflected light of the laser light which is incident in the object and reflected by an opposite surface opposite to a laser light entrance surface; and
a controller configured to control at least the phase pattern to be displayed on the display,
wherein
when the reflected light detector detects the reflected light, the controller sets a phase pattern generated beforehand for correcting aberration generated in an event of the laser light being transmitted through the object having twice the predetermined thickness and displays, on the display, a reflected light aberration correction pattern which is the phase pattern generated beforehand for correcting aberration generated in the event of the laser light being transmitted through the object having twice the predetermined thickness,
the object includes silicon,
the laser light has a wavelength that enables transmission through the object including silicon, and
output of the laser light is adjusted to be at an output smaller than a processing threshold value of the object causing a modified region to not be formed on the object by irradiation of the laser light.

2. The laser light irradiation device according to claim 1, further comprising
the controller configured to determine whether there is a shift between a center position of the entrance pupil plane and a center position of the image of the laser light transferred onto the entrance pupil plane by the image-transfer optical system, based on a detection result of the reflected light detector.

3. The laser light irradiation device according to claim 2, wherein
the reflected light detector comprises a camera configured to capture an image including a point image of the reflected light, and
when the point image of the reflected light in the image captured by the camera is not a rotationally symmetric optical image, the controller determines that there is the shift.

4. The laser light irradiation device according to claim 2, wherein
the reflected light detector comprises a wavefront sensor configured to detect a wavefront of the reflected light, and
when the wavefront of the reflected light detected by the wavefront sensor is not a plane, the controller determines that there is the shift.

5. The laser light irradiation device according to claim 1, further comprising
the controller configured to offset a reference position when the phase pattern is displayed on the display, based on the detection result of the reflected light detector.

6. The laser light irradiation device according to claim 5, wherein the reflected light detector comprises a camera configured to capture an image including a point image of the reflected light, and the controller offsets the reference position such that the point image of the reflected light in the image captured by the camera becomes a rotationally symmetric optical image.

7. The laser light irradiation device according to claim 5, wherein the reflected light detector comprises a wavefront sensor configured to detect a wavefront of the reflected light, and the controller offsets the reference position such that the wavefront of the reflected light detected by the wavefront sensor becomes a plane.

8. The laser light irradiation device according to claim 5, further comprising a movable stage configured to move at least one of the objective lens and the object, wherein the controller executes:

a first process of displaying the reflected light aberration correction pattern on the display;

a second process of moving, by the movable stage, at least one of the objective lens and the object to a position at which the reflected light detector can detect the reflected light;

a third process of, in a state in which the reflected light aberration correction pattern is displayed on the display by the first process after the second process, generating the laser light from the laser light source to irradiate the object and acquiring the detection result of the reflected light detector detected according to the irradiation; and a fourth process of repeating the third process one or more times while changing the position of the reflected light aberration correction pattern on the display and acquiring a plurality of detection results of the reflected light detector, and the controller calculates an optical axis center of the display based on the plurality of detection results of the reflected light detector and offset the reference position to the optical axis center.

9. A laser light irradiation method for irradiating an object having a predetermined thickness with laser light by using a laser light irradiation device, wherein laser light irradiation device includes:

a laser light source configured to generate the laser light;

a spatial light modulator including a display configured to display a phase pattern, the spatial light modulator configured to cause the laser light generated by the laser light source to enter the display, modulate the laser light according to the phase pattern, and emit the laser light from the display;

an objective lens configured to condense the laser light emitted from the spatial light modulator at the object;

an image-transfer optical system configured to transfer an image of the laser light on the display of the spatial light modulator to an entrance pupil plane of the objective lens; and a reflected light detector configured to detect reflected light of the laser light which is incident in the object and reflected by an opposite surface opposite to a laser light entrance surface, the laser light irradiation method comprising:

setting a phase pattern generated beforehand for correcting aberration generated in an event of the laser light being transmitted through the object having twice the predetermined thickness;

displaying, on the display, a reflected light aberration correction pattern which is the phase pattern generated beforehand for correcting aberration generated in the event of the laser light being transmitted through the object having twice the predetermined thickness;

in a state in which the reflected light aberration correction pattern is displayed on the display, generating the laser light from the laser light source to irradiate the object and detecting reflected light of the laser light by the reflected light detector according to the irradiation; and offsetting a reference position serving as a reference when the phase pattern is displayed on the display after the generating the laser light, based on a detection result of the reflected light detector, wherein the object includes silicon, wherein the laser light has a wavelength that enables transmission through the object including silicon, and wherein output of the laser light is adjusted to be at an output smaller than a processing threshold value of the object causing a modified region to not be formed on the object by irradiation of the laser light.

10. The laser light irradiation device according to claim 2, further comprising the controller configured to offset a reference position serving as a reference when the phase pattern is displayed on the display, based on the detection result of the reflected light detector.

11. The laser light irradiation device according to claim 3, further comprising the controller configured to offset a reference position serving as a reference when the phase pattern is displayed on the display, based on the detection result of the reflected light detector.

12. The laser light irradiation device according to claim 4, further comprising the controller configured to offset a reference position serving as a reference when the phase pattern is displayed on the display, based on the detection result of the reflected light detector.

13. The laser light irradiation device according to claim 6, further comprising a movable stage configured to move at least one of the objective lens and the object, wherein the controller executes:

a first process of displaying the reflected light aberration correction pattern on the display;

a second process of moving, by the movable stage, at least one of the objective lens and the object to a position at which the reflected light detector can detect the reflected light;

a third process of, in a state in which the reflected light aberration correction pattern is displayed on the display by the first process after the second process, generating the laser light from the laser light source to irradiate the object and acquiring the detection result of the reflected light detector detected according to the irradiation; and a fourth process of repeating the third process one or more times while changing the position of the reflected light aberration correction pattern on the display and acquiring a plurality of detection results of the reflected light detector, and the controller calculates an optical axis center of the display based on the plurality of detection results of the reflected light detector and offset the reference position to the optical axis center.

14. The laser light irradiation device according to claim 7, further comprising a movable stage configured to move at least one of the objective lens and the object, wherein
the controller executes:
a first process of displaying the reflected light aberration correction pattern on the display;
a second process of moving, by the movable stage, at least one of the objective lens and the object to a position at which the reflected light detector can detect the reflected light;
a third process of, in a state in which the reflected light aberration correction pattern is displayed on the display by the first process after the second process, generating the laser light from the laser light source to irradiate the object and acquiring the detection result of the reflected light detector detected according to the irradiation; and
a fourth process of repeating the third process one or more times while changing the position of the reflected light aberration correction pattern on the display and acquiring a plurality of detection results of the reflected light detector, and
the controller calculates an optical axis center of the display based on the plurality of detection results of the reflected light detector and offset the reference position to the optical axis center.

15. The laser light irradiation device according to claim 10, further comprising
a movable stage configured to move at least one of the objective lens and the object, wherein
the controller executes:
a first process of displaying the reflected light aberration correction pattern on the display;
a second process of moving, by the movable stage, at least one of the objective lens and the object to a position at which the reflected light detector can detect the reflected light;
a third process of, in a state in which the reflected light aberration correction pattern is displayed on the display by the first process after the second process, generating the laser light from the laser light source to irradiate the object and acquiring the detection result of the reflected light detector detected according to the irradiation; and
a fourth process of repeating the third process one or more times while changing the position of the reflected light aberration correction pattern on the display and acquiring a plurality of detection results of the reflected light detector, and
the controller calculates an optical axis center of the display based on the plurality of detection results of the reflected light detector and offset the reference position to the optical axis center.

16. The laser light irradiation device according to claim 11, further comprising
a movable stage configured to move at least one of the objective lens and the object, wherein
the controller executes:
a first process of displaying the reflected light aberration correction pattern on the display;
a second process of moving, by the movable stage, at least one of the objective lens and the object to a position at which the reflected light detector can detect the reflected light;
a third process of, in a state in which the reflected light aberration correction pattern is displayed on the display by the first process after the second process, generating the laser light from the laser light source to irradiate the object and acquiring the detection result of the reflected light detector detected according to the irradiation; and
a fourth process of repeating the third process one or more times while changing the position of the reflected light aberration correction pattern on the display and acquiring a plurality of detection results of the reflected light detector, and
the controller calculates an optical axis center of the display based on the plurality of detection results of the reflected light detector and offset the reference position to the optical axis center.

17. The laser light irradiation device according to claim 12, further comprising
a movable stage configured to move at least one of the objective lens and the object, wherein
the controller executes:
a first process of displaying the reflected light aberration correction pattern on the display;
a second process of moving, by the movable stage, at least one of the objective lens and the object to a position at which the reflected light detector can detect the reflected light;
a third process of, in a state in which the reflected light aberration correction pattern is displayed on the display by the first process after the second process, generating the laser light from the laser light source to irradiate the object and acquiring the detection result of the reflected light detector detected according to the irradiation; and
a fourth process of repeating the third process one or more times while changing the position of the reflected light aberration correction pattern on the display and acquiring a plurality of detection results of the reflected light detector, and
the controller calculates an optical axis center of the display based on the plurality of detection results of the reflected light detector and offset the reference position to the optical axis center.

* * * * *